United States Patent
Ogawa et al.

(10) Patent No.: US 6,320,099 B1
(45) Date of Patent: Nov. 20, 2001

(54) VIRUS RESISTANT PLANTS EXPRESSING ANIMAL CELL-DERIVED (2'-5') OLIGADENYLATE SYNTHETASE AND RIBONUCLEASE L AND A METHOD FOR CREATING THE SAME

(75) Inventors: Toshiya Ogawa; Masaharu Yoshioka; Isao Ishida, all of Kanagawa (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 08/973,005

(22) PCT Filed: May 31, 1996

(86) PCT No.: PCT/JP96/01485

§ 371 Date: Dec. 1, 1997

§ 102(e) Date: Dec. 1, 1997

(87) PCT Pub. No.: WO96/38034

PCT Pub. Date: Dec. 5, 1996

(30) Foreign Application Priority Data

May 31, 1995 (JP) .................................................. 7-133741
Nov. 1, 1995 (JP) .................................................. 7-285401
Mar. 8, 1996 (JP) .................................................. 8-052010

(51) Int. Cl.$^7$ ........................... C12N 15/82; C12N 15/90; A01H 1/00
(52) U.S. Cl. ........................ 800/279; 435/69.1; 435/419; 435/468; 800/288
(58) Field of Search ............................... 435/172.3, 69.1, 435/410, 419, 468; 800/205, 278, 279, 288, 295, 298, 301

(56) References Cited

U.S. PATENT DOCUMENTS

| | | | |
|---|---|---|---|
| 5,491,080 | 2/1996 | Ishida et al. | 435/172.3 |
| 5,589,625 | 12/1996 | Saarma et al. | 800/205 |
| 5,866,787 * | 2/1999 | Silverman et al. | 800/301 |

FOREIGN PATENT DOCUMENTS

| | | |
|---|---|---|
| 84/00466 | 2/1984 | (WO) . |
| WO 93/19187 * | 9/1993 | (WO) . |
| WO 94/20605 * | 9/1994 | (WO) . |

OTHER PUBLICATIONS

SenGupta et al. J. Plant Biochem. Biotech., vol. 5, pp. 69–74, 1996.*
Ishida et al, XVIIIth Eucarpia Symposium, Programme and Book of Abstracts, p. 58, 1995.*
Ishida et al, Acta Horticul., vol. 420, pp. 52–57, 1995.*
Yair Devash, Sara Biggs and Ilan Sela, "Science", vol. 216, No. 4553, Multiplication of Tobacco Mosaic Virus in Tobacco Leaf disks Is Inhibited by (2'–5') Oligoadenylate, pp. 1415–1416, Jun. 1982.
Patent Abstract of WO 94/20605, Sep. 1994.
Patent Abstract of WO 95/22245, Aug. 1995.
Patent Abstract of WO 96/39806, Dec. 1996.
Gadani, et al., "Genetic Engineering of Plants for Virus Resistance", Arch. Virol., (1990) 115: 1–21.
Truve et al., "Transgenic Potato Plants Expressing Mammalian 2'–5' Oligoadenylate Synthetase Protected From Potato Virus X Infection Under Field Conditions", Bio/Technology, (19930, 11: 1048–1052.
Ishida et al., "Production of Plants Tolerant to Multiple Viral Infections by Genetic Manipulations", Acta Horticulture 420, (1995) 52–57.
Cayley et al., "Distribution of the ppp(A2'p)$_n$A–binding protein and interferon–related enzymes in animals, plants, and lower organisms", Biochem. Biophys. Res. Commun., (1982) 108: 1243–1250.
Devash et al., "5'–Dephosphorylated 2'5'–Adenylate Trimer Its Analogs", J. Biol. Chem., (1984) 259: 3482–3486.
Lengyel, "Biochemistry of Interferons and their Actions", Ann. Rev. Biochem., (1982) 51: 251–282.
Benech et al., "Structure of the Two Forms of the Interferon–induced (2'5') Oligo A Synthesis of Human Cells Based on cDNAs and Gene Sequences", EMBO J., (1985) 4: 2249–2256.
Ghosh et al., "Cloning, Sequencing, and Expression of Two Murine 2'–5'–Oligoadenylate Synthetases", J. Biol. Chem., (1991) 266: 15293–15299.
Rutherford et al., "The Murain 2–5A Synthetase Locus: Three Distinct Transcripts from Two Linked Genes", Nucleic Acids Research, (1991) 19: 1917–1924.
Zhou et al., "Expression Cloning of 2–5A–Dependent RNAase: A Uniquely Regulated Mediator of Interferon action", Cell, (1993) 72: 753–765.
Merlin et al., "Molecular Cloning and Sequence of Partial cDNA for Interferon–induced (2'5')Oligo(A) Synthetase mRNa from Human Cells", Proc. Natl. Acad. Sci. USA., (1983) 80: 4904–4308.
Coccia et al., "A Full–Length Murine 2–5A Synthetase cDNa Transfected in NIH–3T3 Cels Impairs EMCV but not VSV Repliction", Virology, (1990) 179: 228–233.
Schröder et la., "Modulation of Nuclear Matrix–associated 2',5'–Oligoadenylate Metabolism and Ribonuclease L Activity in H9 Cells by Human Immunodeficiency Virus", J. Biol. Chem., (1989) 264: 5669–5673.
"Biochemistry Encyclopedia", by Tokyo Kagaku Dojin, (1990) p. 236, Section of (2'–5')Oligoadenylate and p. 1423, Section of Ribonuclease L, and the Corresponding English Translation XVIIIthe Eucarpia Symposium Section Ornamentals, (1995) p. 58.
Truve et al., "Principles and Background for the Construction of Transgenic Plants Displaying Multiple Virus Resistance", Arch. Virol., (1994) 9: 41–50.

* cited by examiner

Primary Examiner—Elizabeth F. McElwain
Assistant Examiner—Ashwin Mehta
(74) Attorney, Agent, or Firm—Foley & Lardner

(57) ABSTRACT

The present invention relates to a method for creating a plant having resistance to RNA viruses, comprising incorporating a DNA sequence encoding an animal cell-derived (2'-5') oligoadenylate synthetase and a DNA sequence encoding an animal cell-derived ribonuclease L into a chromosome(s) of the plant and expressing the DNA sequences, as well as plants created by the above method. The present invention is widely applicable to the breeding of virus resistant plant varieties.

7 Claims, 35 Drawing Sheets

(19 of 35 Drawing Sheet(s) Filed in Color)

FIG. 1
pB12-SAase
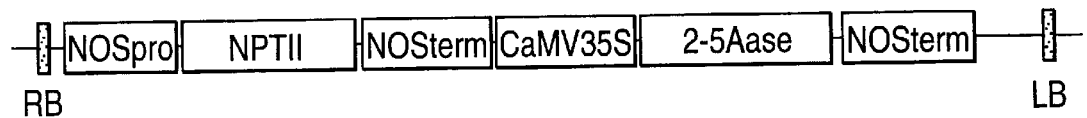
pBIBRNaseL(T)
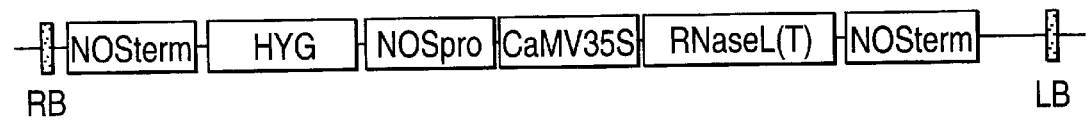
pBIBRNaseL(F)
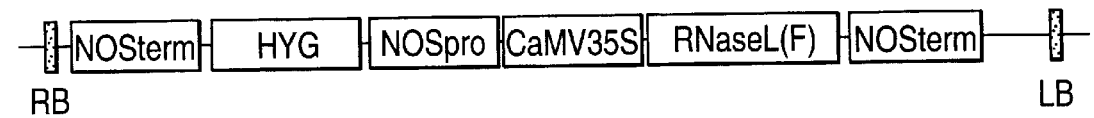
FIG. 2
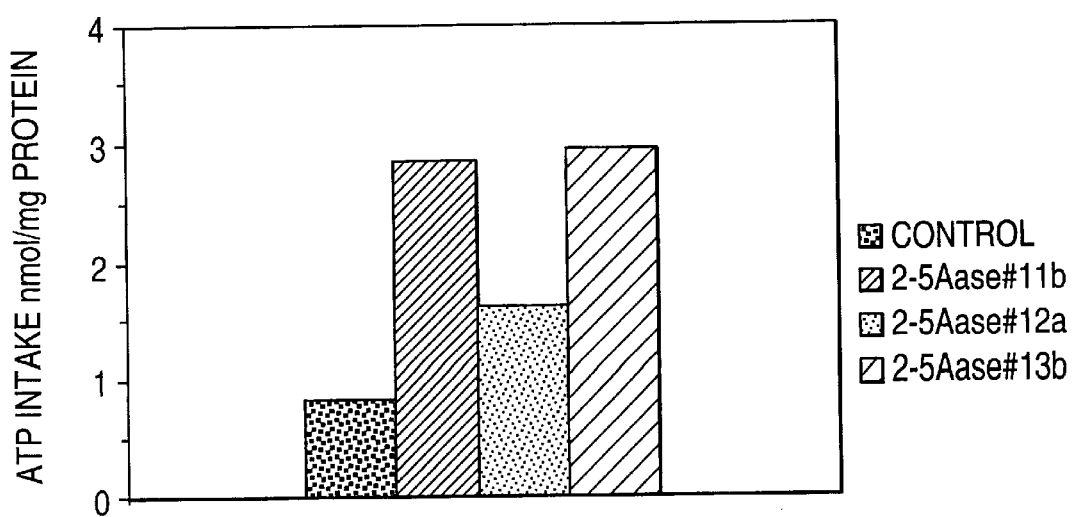

FIG. 7A
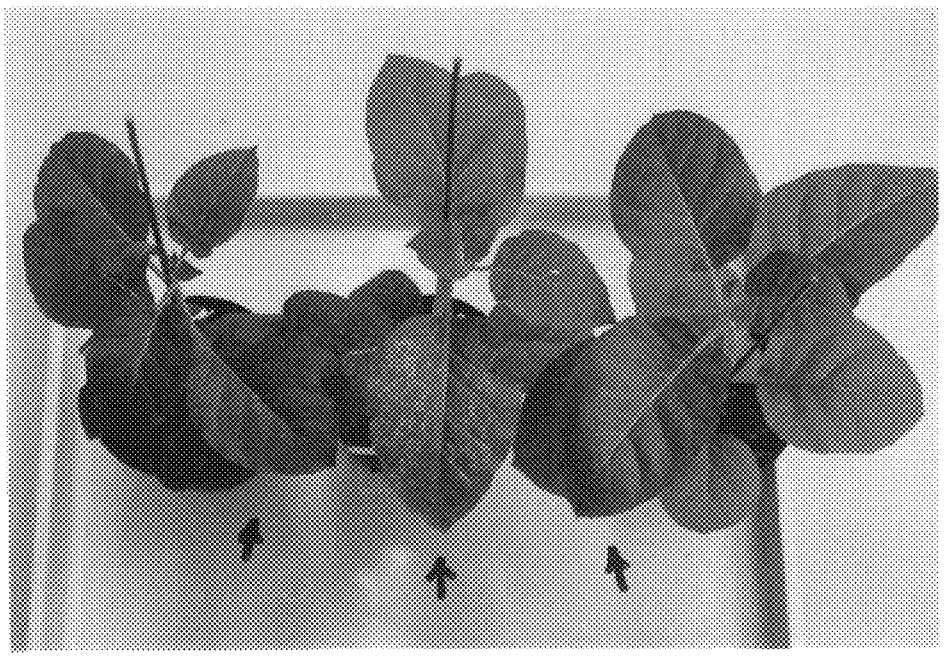
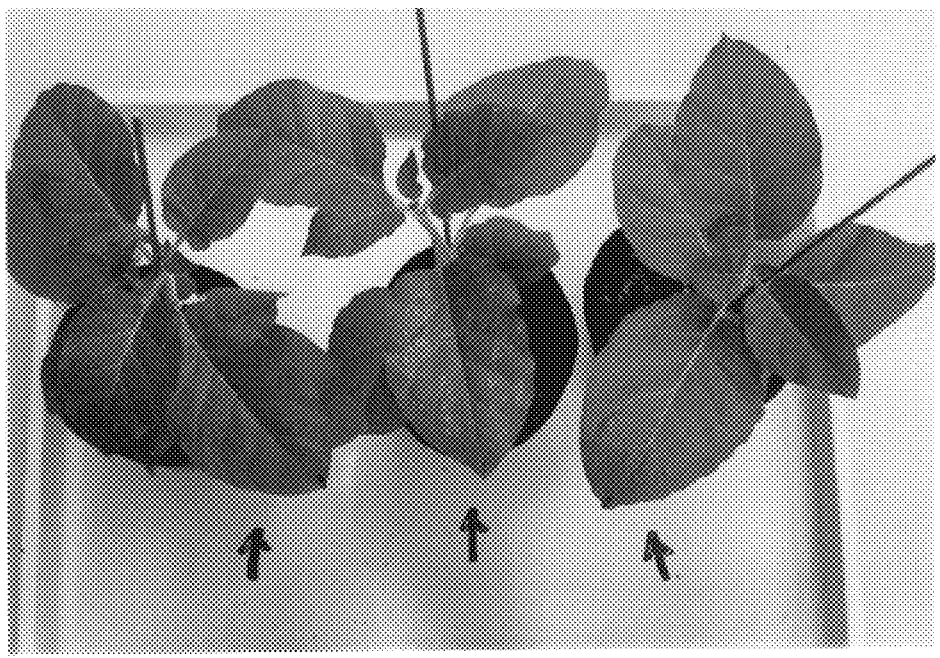

FIG. 8A
A  B  C
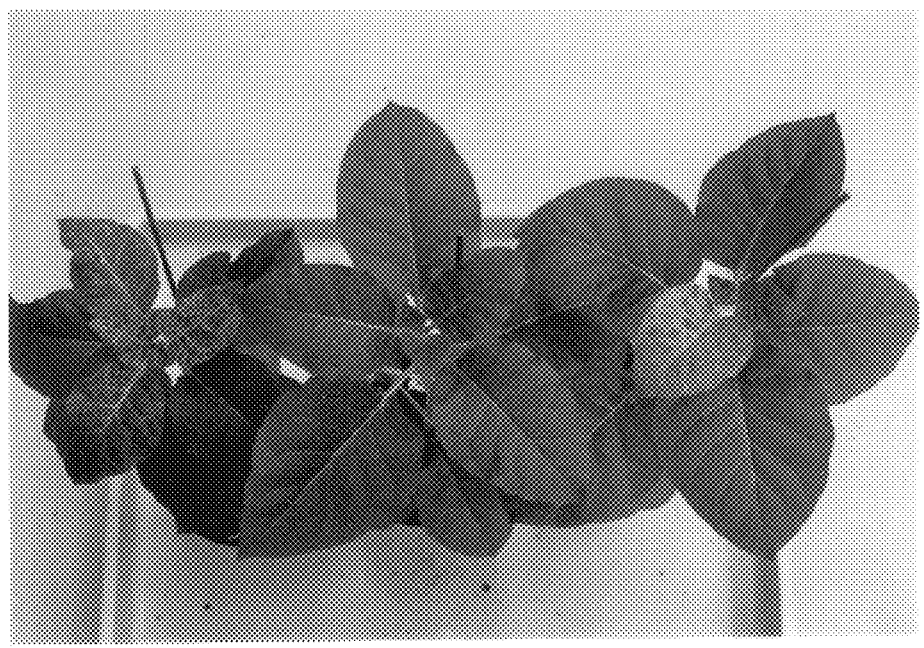
D  E  F
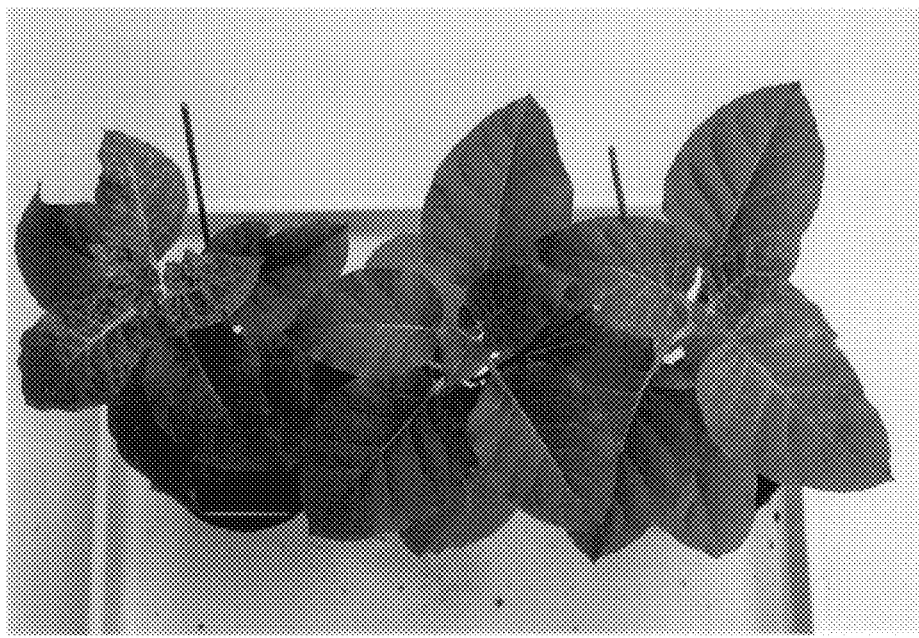

G　　　H　　　I

FIG. 11
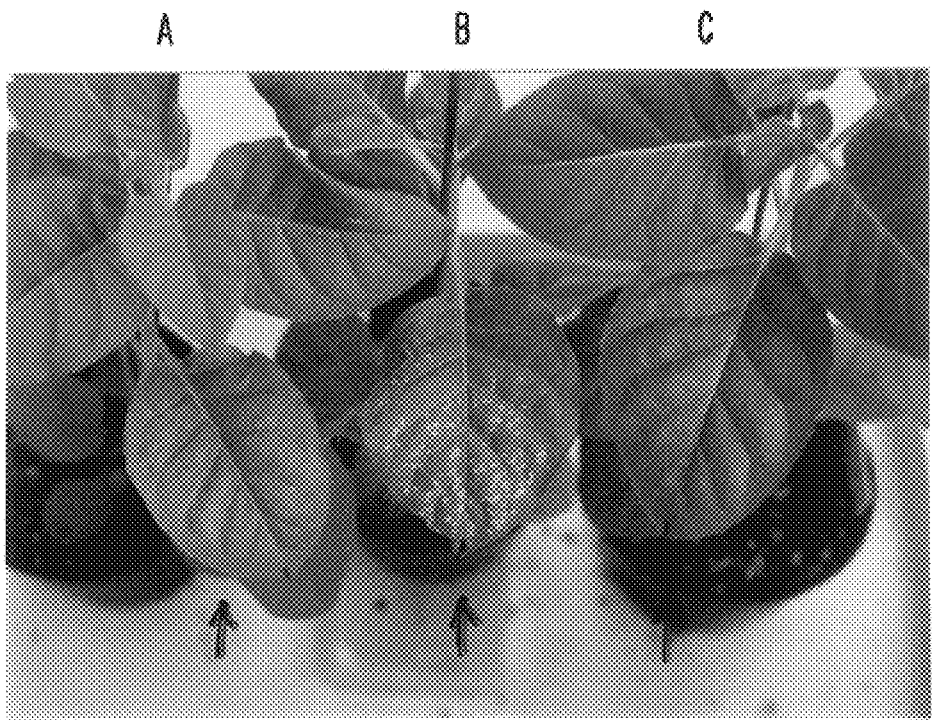
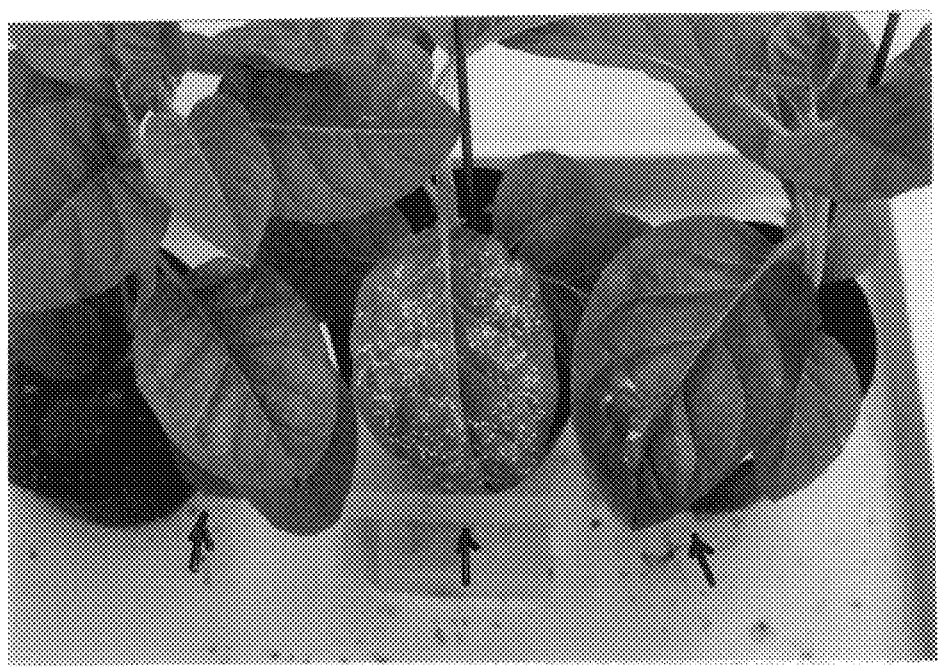

FIG. 12
A	B	C
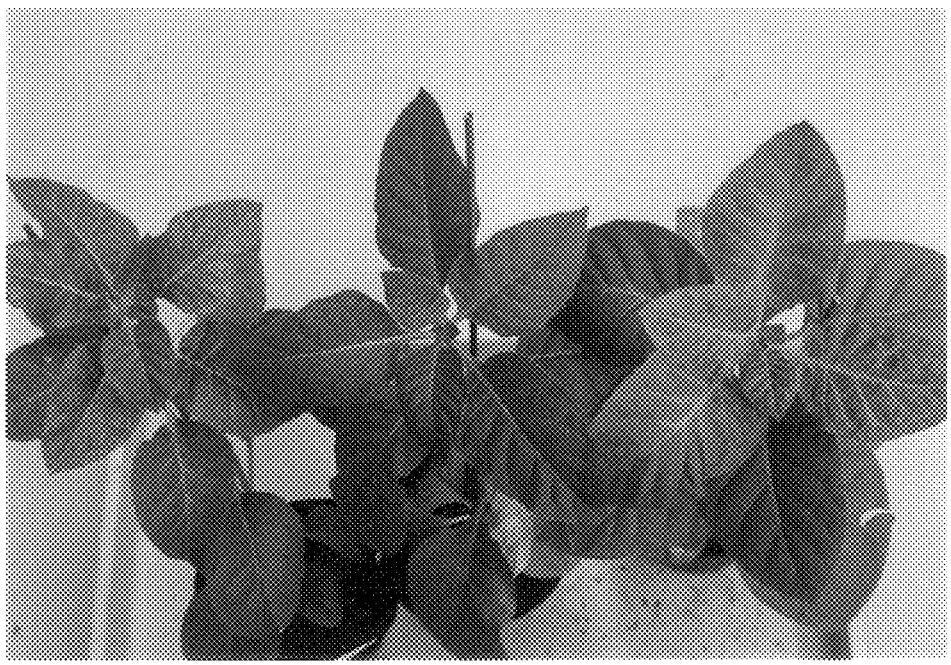
D	E	F
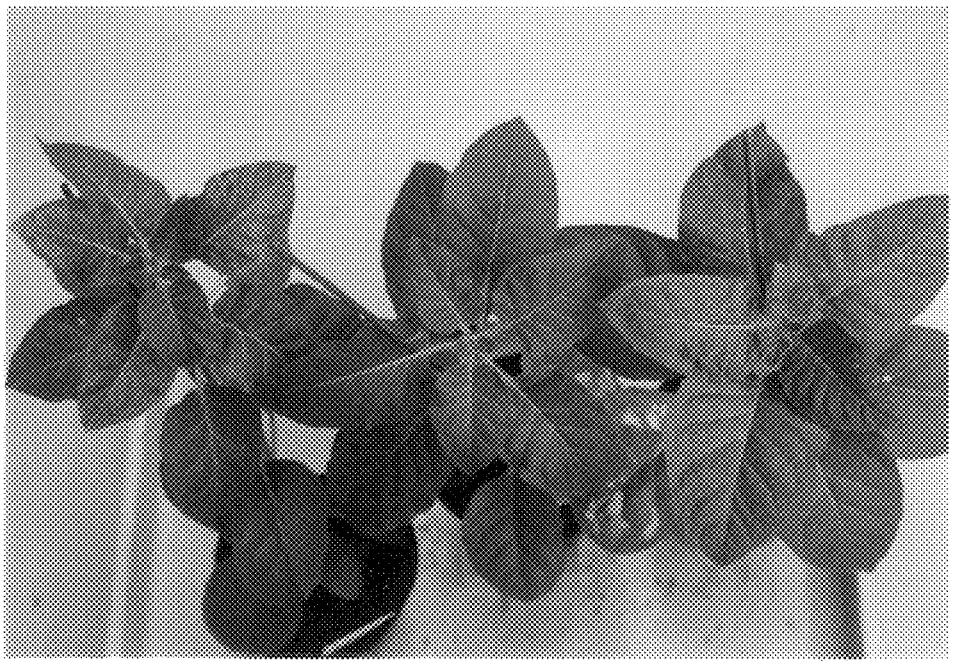

FIG. 13
A B C
D E F

FIG. 14A
A  B  C
D  E  F
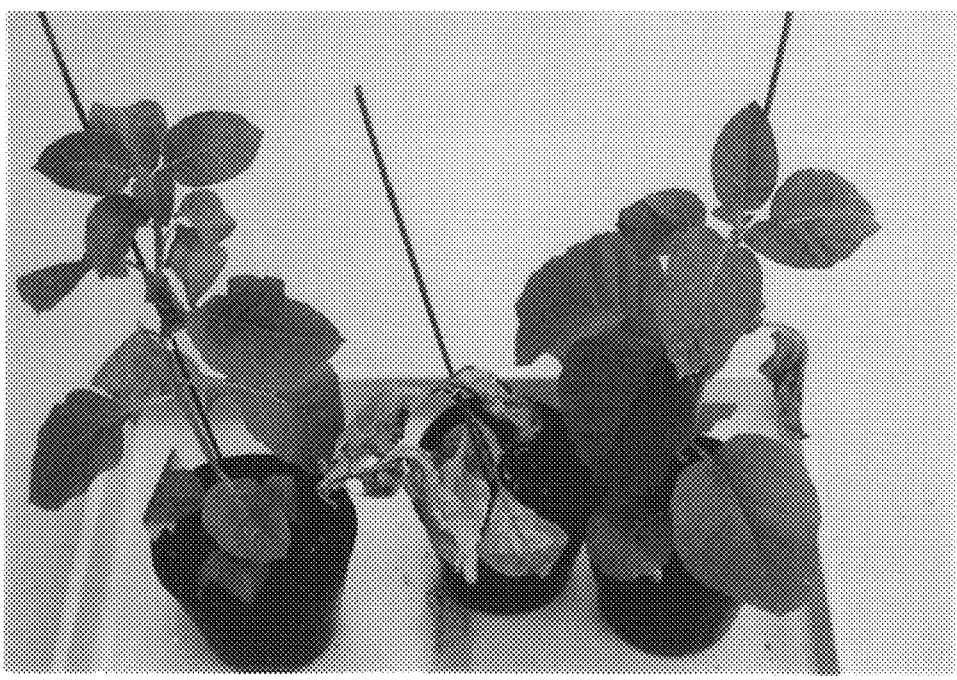

FIG. 16A
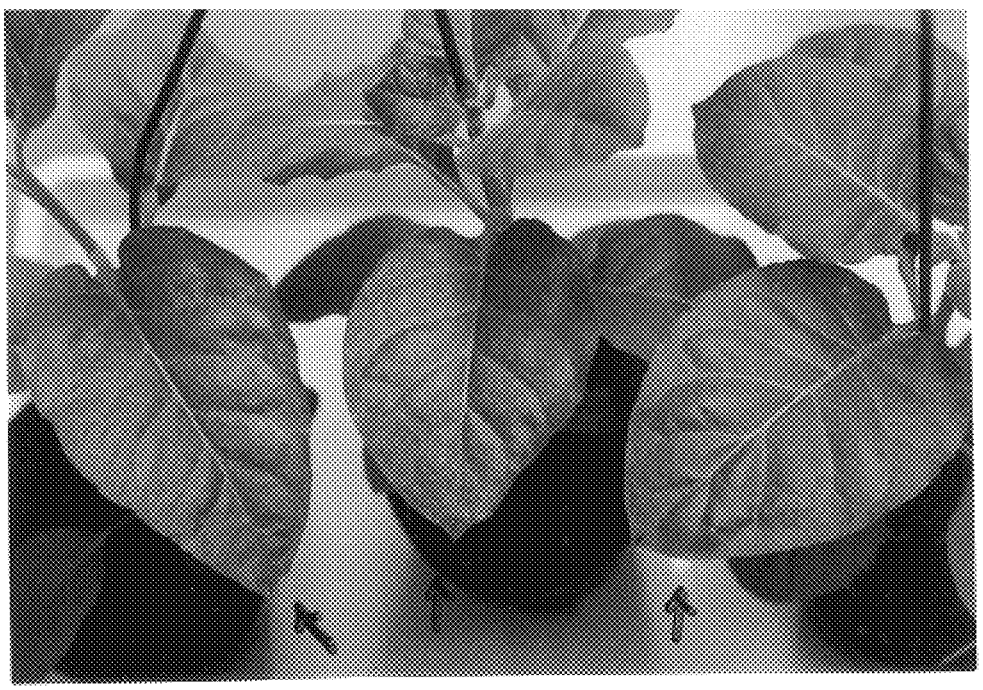
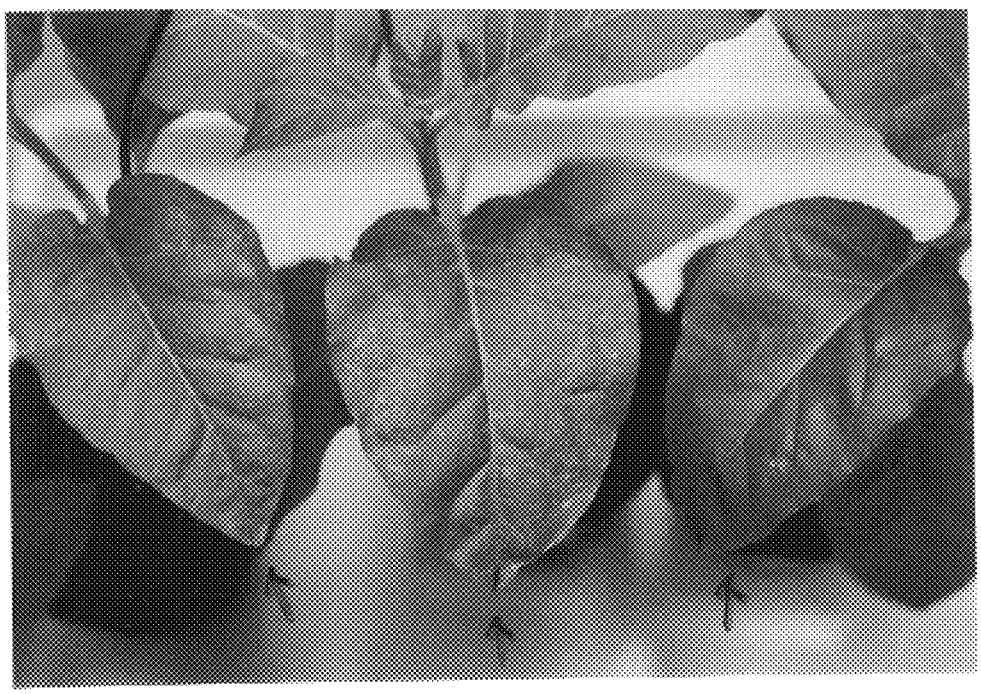

FIG. 17A
A  B  C
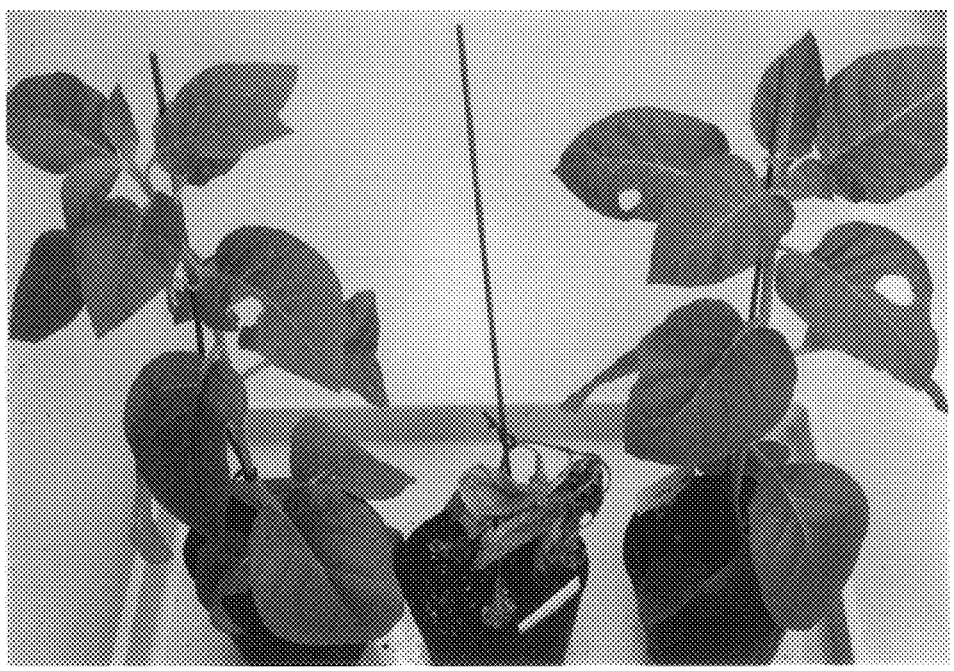
D  E  F

```
         9          18          27          36          45          54
5' ATG GAA CTC AGA TAT ACC CCG GCC GGG TCT CTA GAC AAG TTC ATC CAA GTC CAC
   --- --- --- --- --- --- --- --- --- --- --- --- --- --- --- --- --- ---
    M   E   L   R   Y   T   P   A   G   S   L   D   K   F   I   Q   V   H 63          72          81          90          99         108
   CTC CTG CCA AAC GAA GAA TTC AGC ACG CAG GTC CAA GAA GCC ATC GAC ATC ATC
   --- --- --- --- --- --- --- --- --- --- --- --- --- --- --- --- --- ---
    L   L   P   N   E   E   F   S   T   Q   V   Q   E   A   I   D   I   I 117         126         135         144         153         162
   TGC ACT TTC CTG AAG GAA AAG TGT TTC CGA TGT GCC CCT CAC AGA GTT CGG GTG
   --- --- --- --- --- --- --- --- --- --- --- --- --- --- --- --- --- ---
    C   T   F   L   K   E   K   C   F   R   C   A   P   H   R   V   R   V 171         180         189         198         207         216
   TCC AAA GTT GTG AAG GGC GGC TCC TCA GGC AAA GGC ACG ACC CTC AGG GGA CGA
   --- --- --- --- --- --- --- --- --- --- --- --- --- --- --- --- --- ---
    S   K   V   V   K   G   G   S   S   G   K   G   T   T   L   R   G   R 225         234         243         252         261         270
   TCA GAT GCT GAC CTC GTC GTC TTC CTC ACC AAT CTC ACA AGT TTT CAG GAA CAG
   --- --- --- --- --- --- --- --- --- --- --- --- --- --- --- --- --- ---
    S   D   A   D   L   V   V   F   L   T   N   L   T   S   F   Q   E   Q 279         288         297         306         315         324
   CTT GAG CGC CGA GGA GAA TTC ATT GAA GAA ATC AGG AGA CAG CTG GAA GCC TGT
   --- --- --- --- --- --- --- --- --- --- --- --- --- --- --- --- --- ---
    L   E   R   R   G   E   F   I   E   E   I   R   R   Q   L   E   A   C 333         342         351         360         369         378
   CAA AGA GAG GAA ACA TTT GAA GTG AAG TTT GAG GTC CAG AAA CGG CAA TGG GAG
   --- --- --- --- --- --- --- --- --- --- --- --- --- --- --- --- --- ---
    Q   R   E   E   T   F   E   V   K   F   E   V   Q   K   R   Q   W   E
```

FIG. 19B

```
      387         396         405         414         423         432
AAT CCC CGC GCT CTC AGC TTT GTG CTG AGG TCC CCC AAG CTC AAC CAG GCG GTG
--- --- --- --- --- --- --- --- --- --- --- --- --- --- --- --- --- ---
 N   P   R   A   L   S   F   V   L   R   S   P   K   L   N   Q   A   V 441         450         459         468         477         486
GAG TTC TAT GTC CTG CCC GCC TTT GAT GCC CTA GGT CAG TTG ACC AAA GGT TAC
--- --- --- --- --- --- --- --- --- --- --- --- --- --- --- --- --- ---
 E   F   Y   V   L   P   A   F   D   A   L   G   Q   L   T   K   G   Y 495         504         513         522         531         540
AGA CCT GAC TCT AGA GTC TAT GTC CGG CTC ATC CAA GAG TGC GAG AAC CTG AGG
--- --- --- --- --- --- --- --- --- --- --- --- --- --- --- --- --- ---
 R   P   D   S   R   V   Y   V   R   L   I   Q   E   C   E   N   L   R 549         558         567         576         585         594
AGA GAG GGC GAG TTC TCC CCC TGC TTC ACG GAG CTG CAG CGA GAC TTC CTG AAG
--- --- --- --- --- --- --- --- --- --- --- --- --- --- --- --- --- ---
 R   E   G   E   F   S   P   C   F   T   E   L   Q   R   D   F   L   K 603         612         621         630         639         648
AAT CGT CCA ACC AAG CTG AAG AAC CTC ATC CGC CTG GTG AAG CAC TGG TAC CAA
--- --- --- --- --- --- --- --- --- --- --- --- --- --- --- --- --- ---
 N   R   P   T   K   L   K   N   L   I   R   L   V   K   H   W   Y   Q 657         666         675         684         693         702
CTG TGT AAG GAG CAG CTT GGA AAG CCA TTG CCC CCA CAA TAT GCT CTG GAG CTT
--- --- --- --- --- --- --- --- --- --- --- --- --- --- --- --- --- ---
 L   C   K   E   Q   L   G   K   P   L   P   P   Q   Y   A   L   E   L
```

FIG. 19C

```
     711         720         729         738         747         756
CTG ACG GTC TAT GCC TGG GAA CAA GGA TGC AAT AAA ACA GGA TTC ATC ACA GCT
--- --- --- --- --- --- --- --- --- --- --- --- --- --- --- --- --- ---
 L   T   V   Y   A   W   E   Q   G   C   N   K   T   G   F   I   T   A 765         774         783         792         801         810
CAG GGA TTT CAG ACT GTC TTG AAA TTA GTC CTA AAG TAT CAG AAG CTT TGC ATC
--- --- --- --- --- --- --- --- --- --- --- --- --- --- --- --- --- ---
 Q   G   F   Q   T   V   L   K   L   V   L   K   Y   Q   K   L   C   I 819         828         837         846         855         864
TAC TGG GAA AAG AAC TAT AAC TCT GAA AAC CCT ATT ATT GAA GAA TAT CTG ACG
--- --- --- --- --- --- --- --- --- --- --- --- --- --- --- --- --- ---
 Y   W   E   K   N   Y   N   S   E   N   P   I   I   E   E   Y   L   T 873         882         891         900         909         918
AAG CAA CTT GCA AAA CCC AGG CCT GTG ATT CTG GAC CCG GCG GAC CCT ACA GGA
--- --- --- --- --- --- --- --- --- --- --- --- --- --- --- --- --- ---
 K   Q   L   A   K   P   R   P   V   I   L   D   P   A   D   P   T   G 927         936         945         954         963         972
AAT GTT GCT GGT AAA GAC GCA TAT AGC TGG GAA CGG CTT GCA CGA ACG GCT TTG
--- --- --- --- --- --- --- --- --- --- --- --- --- --- --- --- --- ---
 N   V   A   G   K   D   A   Y   S   W   E   R   L   A   R   T   A   L 981         990         999         1008        1017        1026
GTC TGG CTG GAT TAC CCG TGC TTT AAG AAA TGG GAT GGG TCT CCC GTG GGC TCC
--- --- --- --- --- --- --- --- --- --- --- --- --- --- --- --- --- ---
 V   W   L   D   Y   P   C   F   K   K   W   D   G   S   P   V   G   S
```

FIG. 19D

```
      1035            1044            1053            1062            1071            1080
TGG  GAT  GTG  TCG  CCC  CAA  GAA  CAC  AGT  GAC  CTG  ATG  TTC  CAG  GCC  TAT  GAT  TTT
---  ---  ---  ---  ---  ---  ---  ---  ---  ---  ---  ---  ---  ---  ---  ---  ---  ---
 W    D    V    S    P    Q    E    H    S    D    L    M    F    Q    A    Y    D    F 1089            1098            1107            1116            1125            1134
AGA  CAG  CAC  TAT  AGA  CCC  TCT  CCA  GGA  ATC  CAG  TTC  CAC  GGA  GGA  GCC  TCT  CCC
---  ---  ---  ---  ---  ---  ---  ---  ---  ---  ---  ---  ---  ---  ---  ---  ---  ---
 R    Q    H    Y    R    P    S    P    G    I    Q    F    H    G    G    A    S    P 1143            1152            1161            1170
CAG  GTG  GAA  GAG  AAC  TGG  ACA  TGT  ACC  ATC  CTC  TGA  3'
---  ---  ---  ---  ---  ---  ---  ---  ---  ---  ---  ---
 Q    V    E    E    N    W    T    C    T    I    L    *
```

FIG. 20A

```
           9              18             27             36             45             54
5' ATG GAG ACT GAG AGC CAT AAC AAC CCT CAG GAA AGA CCC ACA CCC TCT AGT AAT
   --- --- --- --- --- --- --- --- --- --- --- --- --- --- --- --- --- ---
    M   E   T   E   S   H   N   N   P   Q   E   R   P   T   P   S   S   N 63             72             81             90             99            108
   GGG AAG GCT TCA ATG GGA GAC AAT CAT TCG TTG ATT AAA GCT GTT AGA GAT GAA
   --- --- --- --- --- --- --- --- --- --- --- --- --- --- --- --- --- ---
    G   K   A   S   M   G   D   N   H   S   L   I   K   A   V   R   D   E 117            126            135            144            153            162
   GAC ATT GAG TCG GTC CAG CAA TTG CTA GAA AGA GGG GCT GAT GTC AAT TTC CAG
   --- --- --- --- --- --- --- --- --- --- --- --- --- --- --- --- --- ---
    D   I   E   S   V   Q   Q   L   L   E   R   G   A   D   V   N   F   Q 171            180            189            198            207            216
   GAA GAA TGG GGC TGG TCA CCT TTG CAT AAT GCA GTA CAA GTT GAC AGA GAG GAC
   --- --- --- --- --- --- --- --- --- --- --- --- --- --- --- --- --- ---
    E   E   W   G   W   S   P   L   H   N   A   V   Q   V   D   R   E   D 225            234            243            252            261            270
   ATT GTG GAA CTT CTG CTT AGT CAT GGT GCT GAG CCT TGT CTG CGG AAG AAG AAT
   --- --- --- --- --- --- --- --- --- --- --- --- --- --- --- --- --- ---
    I   V   E   L   L   L   S   H   G   A   E   P   C   L   R   K   K   N 279            288            297            306            315            324
   GGG GCC ACT CCC TTC ATC ATT GCT GGG ATT GTG GGA AAC GTG AAG TTG CTC AAA
   --- --- --- --- --- --- --- --- --- --- --- --- --- --- --- --- --- ---
    G   A   T   P   F   I   I   A   G   I   V   G   N   V   K   L   L   K 333            342            351            360            369            378
   CTA TTA CTT CCT AAA GTA ACA GAT GTC AAT GAG TGT GAT GTT AAT GGC TTC ACA
   --- --- --- --- --- --- --- --- --- --- --- --- --- --- --- --- --- ---
    L   L   L   P   K   V   T   D   V   N   E   C   D   V   N   G   F   T
```

FIG. 20B

```
      387         396         405         414         423         432
GCT TTC ATG GAA GCT GCT GTG TAT GGC AAA GTC GAA GCC TTA AGA TTC CTG TAT
--- --- --- --- --- --- --- --- --- --- --- --- --- --- --- --- --- ---
 A   F   M   E   A   A   V   Y   G   K   V   E   A   L   R   F   L   Y 441         450         459         468         477         486
AAC AAC GGA GCA GAG GTG AAT TTG CAC AGA AAG ACA ATA GAG GAT CAA GAG AGG
--- --- --- --- --- --- --- --- --- --- --- --- --- --- --- --- --- ---
 N   N   G   A   E   V   N   L   H   R   K   T   I   E   D   Q   E   R 495         504         513         522         531         540
GTT AAG AAA GGA GGG GCC ACT GCT CTC ATG GAT GCT GCT AGA AGA GGG CAT GTA
--- --- --- --- --- --- --- --- --- --- --- --- --- --- --- --- --- ---
 V   K   K   G   G   A   T   A   L   M   D   A   A   R   R   G   H   V 549         558         567         576         585         594
GAT GTC GTA GAG ATC CTC CTT CAT GAG ATG GGG GCA GAT GTC AAT GCT CGG GAC
--- --- --- --- --- --- --- --- --- --- --- --- --- --- --- --- --- ---
 D   V   V   E   I   L   L   H   E   M   G   A   D   V   N   A   R   D 603         612         621         630         639         648
AAT AGG GGC AGA AAT GCT TTA ATC TAT GCT CTT CTG AAC TCT GAT GAT GAG AAG
--- --- --- --- --- --- --- --- --- --- --- --- --- --- --- --- --- ---
 N   R   G   R   N   A   L   I   Y   A   L   L   N   S   D   D   E   K 657         666         675         684         693         702
GTG AAA GTG AAA GCN ACT ACT CGC CTT CTG CTG GAC TAT AAG GTT GAT GTC AAT
--- --- --- --- --- --- --- --- --- --- --- --- --- --- --- --- --- ---
 V   K   V   K   A   T   T   R   L   L   L   D   Y   K   V   D   V   N
```

FIG. 20C

```
     711         720         729         738         747         756
GTG AGG GGG GAA GGA AGG AAG ACG CCG CTG ATC TTG GCA GTG GAA AAG AAG AAC
--- --- --- --- --- --- --- --- --- --- --- --- --- --- --- --- --- ---
 V   R   G   E   G   R   K   T   P   L   I   L   A   V   E   K   K   N 765         774         783         792         801         810
CTG GAT CTG GTG CAG ATG CTT CTG GAA CAA ACA GCT ATA GAG ATT AAT GAC ACA
--- --- --- --- --- --- --- --- --- --- --- --- --- --- --- --- --- ---
 L   D   L   V   Q   M   L   L   E   Q   T   A   I   E   I   N   D   T 819         828         837         846         855         864
GAC AGT GAG GGT AAA ACA GCA CTG CTG CTT GCT GTC GAG CTC AAG CTG AAG GAA
--- --- --- --- --- --- --- --- --- --- --- --- --- --- --- --- --- ---
 D   S   E   G   K   T   A   L   L   L   A   V   E   L   K   L   K   E 873         882         891         900         909         918
ATT GCC CAG TTG CTG TGT CGC AAA GGA GCC AGC ACA AAA TGC GGG GAC CTC GTC
--- --- --- --- --- --- --- --- --- --- --- --- --- --- --- --- --- ---
 I   A   Q   L   L   C   R   K   G   A   S   T   K   C   G   D   L   V 927         936         945         954         963         972
GCA ATA GCG AAG CGC AAT TAT GAC TCT GAC CTT GCA AAG TTC CTT CGC CAG CAT
--- --- --- --- --- --- --- --- --- --- --- --- --- --- --- --- --- ---
 A   I   A   K   R   N   Y   D   S   D   L   A   K   F   L   R   Q   H 981         990         999        1008        1017        1026
GGA GCT GTA GAA GAC GTT TGC CCT CCT GCT AAA GCC TGG AAG CCT CAG AGC TCA
--- --- --- --- --- --- --- --- --- --- --- --- --- --- --- --- --- ---
 G   A   V   E   D   V   C   P   P   A   K   A   W   K   P   Q   S   S 1035        1044        1053        1062        1071        1080
CGT TGG GGG GAG GCC CTG AAA CAT CTT CAC AGG ATA TAC CGC CCT ATG ATA GGC
--- --- --- --- --- --- --- --- --- --- --- --- --- --- --- --- --- ---
 R   W   G   E   A   L   K   H   L   H   R   I   Y   R   P   M   I   G
```

FIG. 20D

```
        1089           1098           1107           1116           1125           1134
AAA CTC AAG ATC TTT ATT GAT GAA GAA TAT AAA ATC GCT GAC ACT TCC CAA GGG
--- --- --- --- --- --- --- --- --- --- --- --- --- --- --- --- --- ---
 K   L   K   I   F   I   D   E   E   Y   K   I   A   D   T   S   Q   G 1143           1152           1161           1170           1179           1188
GGC ATC TAC CTG GGG TTA TAT GAG GAA CAA GAG GTA GCT GTG AAG CGG TTC CCT
--- --- --- --- --- --- --- --- --- --- --- --- --- --- --- --- --- ---
 G   I   Y   L   G   L   Y   E   E   Q   E   V   A   V   K   R   F   P 1197           1206           1215           1224           1233           1242
AAA GGC AGC ACA CGG GGA CAA AAT GAA GTC TCT TGT TTG CAG AGC AAC CGA GCC
--- --- --- --- --- --- --- --- --- --- --- --- --- --- --- --- --- ---
 K   G   S   T   R   G   Q   N   E   V   S   C   L   Q   S   N   R   A 1251           1260           1269           1278           1287           1296
AAT GGT CAC GTG GTG ACG TTC TAT GGC AGT GAG AGC GAC AGG ACC TGT CTG TAT
--- --- --- --- --- --- --- --- --- --- --- --- --- --- --- --- --- ---
 N   G   H   V   V   T   F   Y   G   S   E   S   D   R   T   C   L   Y 1305           1314           1323           1332           1341           1350
GTG TGC CTT GCC CTG TGT GAG CAC ACG CTG GAG AAG CAC TTG GAC GAC CGC AAA
--- --- --- --- --- --- --- --- --- --- --- --- --- --- --- --- --- ---
 V   C   L   A   L   C   E   H   T   L   E   K   H   L   D   D   R   K 1359           1368           1377           1386           1395           1404
GGA GAG GCT GTG CAA AAC AAG GAA GAT GAA TTT GCC CGC AAC ATC CTC TCA TCT
--- --- --- --- --- --- --- --- --- --- --- --- --- --- --- --- --- ---
 G   E   A   V   Q   N   K   E   D   E   F   A   R   N   I   L   S   S 1413           1422           1431           1440           1449           1458
CTG TTT AAG GCT GTT GAG GAA CTA CAC CGG TCT GGA TAC ACT CAT CAG GAT CTG
--- --- --- --- --- --- --- --- --- --- --- --- --- --- --- --- --- ---
 L   F   K   A   V   E   E   L   H   R   S   G   Y   T   H   Q   D   L
```

FIG. 20E

```
       1467           1476           1485           1494           1503           1512
CAA CCG CAG AAC ATC TTA ATA GAT TCC AAG AAT GGT GCT TGC CTG GCA GAT TTT
--- --- --- --- --- --- --- --- --- --- --- --- --- --- --- --- --- ---
 Q   P   Q   N   I   L   I   D   S   K   N   G   A   C   L   A   D   F 1521           1530           1539           1548           1557           1566
GAT AAA AGC GTC AAG GGG ACT GGA GAT CCA CAG GAA ATC AAG AGA GAT CTA GAG
--- --- --- --- --- --- --- --- --- --- --- --- --- --- --- --- --- ---
 D   K   S   V   K   G   T   G   D   P   Q   E   I   K   R   D   L   E 1575           1584           1593           1602           1611           1620
GCC CTG GGA CTG CTG GTC CTA TAT GTG GTA AAA AAG GGA AAT GAT TCT TTT GAG
--- --- --- --- --- --- --- --- --- --- --- --- --- --- --- --- --- ---
 A   L   G   L   L   V   L   Y   V   V   K   K   G   N   D   S   F   E 1629           1638           1647           1656           1665           1674
ATG CTG AAG AAT CTA AGA ACT GAA GAG TTG ATT GAG CGT TCT CCA GAT AAG GAA
--- --- --- --- --- --- --- --- --- --- --- --- --- --- --- --- --- ---
 M   L   K   N   L   R   T   E   E   L   I   E   R   S   P   D   K   E 1683           1692           1701           1710           1719           1728
ACT CGG GAC CTC ATT CGG CAT CTG TTA GTC CCT GGG GAC AAT GTG AAG GGC CAT
--- --- --- --- --- --- --- --- --- --- --- --- --- --- --- --- --- ---
 T   R   D   L   I   R   H   L   L   V   P   G   D   N   V   K   G   H 1737           1746           1755           1764           1773           1782
CTG AGT GGC CTG CTG GCT CAT CCC TTC TTT TGG AGT TGG GAG AGC CGC TAC CGG
--- --- --- --- --- --- --- --- --- --- --- --- --- --- --- --- --- ---
 L   S   G   L   L   A   H   P   F   F   W   S   W   E   S   R   Y   R 1791           1800           1809           1818           1827           1836
ACC CTA CGG GAT GTG GGA AAC GAA TCT GAC ATC AAA ACA CGA AAT ACT AAT GGC
--- --- --- --- --- --- --- --- --- --- --- --- --- --- --- --- --- ---
 T   L   R   D   V   G   N   E   S   D   I   K   T   R   N   T   N   G
```

FIG. 20F

```
      1845        1854        1863        1872        1881        1890
AAG ATC CTC CAG CTT CTG CAA CCT GAA ACA TCT GAA CTT CCA AGT TTT GCC CAG
--- --- --- --- --- --- --- --- --- --- --- --- --- --- --- --- --- ---
 K   I   L   Q   L   L   Q   P   E   T   S   E   L   P   S   F   A   Q 1899        1908        1917        1926        1935        1944
TGG ACA ATT GAG GTT GAC AAA TCT GTG ATG AAA AAA ATG AAT ACC TAT CAG AAC
--- --- --- --- --- --- --- --- --- --- --- --- --- --- --- --- --- ---
 W   T   I   E   V   D   K   S   V   M   K   K   M   N   T   Y   Q   N 1953        1962        1971        1980        1989        1998
ACT GTA GGT GAC CTG CTG AAG TTC ATC CGG AAT GTG GGA GAG CAC ATT AAT GAA
--- --- --- --- --- --- --- --- --- --- --- --- --- --- --- --- --- ---
 T   V   G   D   L   L   K   F   I   R   N   V   G   E   H   I   N   E 2007        2016        2025        2034        2043        2052
CAA AAG AAT ATA GAG ATG AAG TCA AAA ATT GGA GAA CCT TCC CAG TAT TTT CAG
--- --- --- --- --- --- --- --- --- --- --- --- --- --- --- --- --- ---
 Q   K   N   I   E   M   K   S   K   I   G   E   P   S   Q   Y   F   Q 2061        2070        2079        2088        2097        2106
GAG AAA TTT CCA GAT CTG GTC ATG TAT GTC TAT AAA AGA CTA CAG AAC ACA GAA
--- --- --- --- --- --- --- --- --- --- --- --- --- --- --- --- --- ---
 E   K   F   P   D   L   V   M   Y   V   Y   K   R   L   Q   N   T   E 2115        2124        2133        2142        2151
TAT GCA AAG CAT TTT CCA AAA AAT CTC AAC CTG AAC AAA CCC GAC GTG TGA 3'
--- --- --- --- --- --- --- --- --- --- --- --- --- --- --- --- ---
 Y   A   K   H   F   P   K   N   L   N   L   N   K   P   D   V   *
```

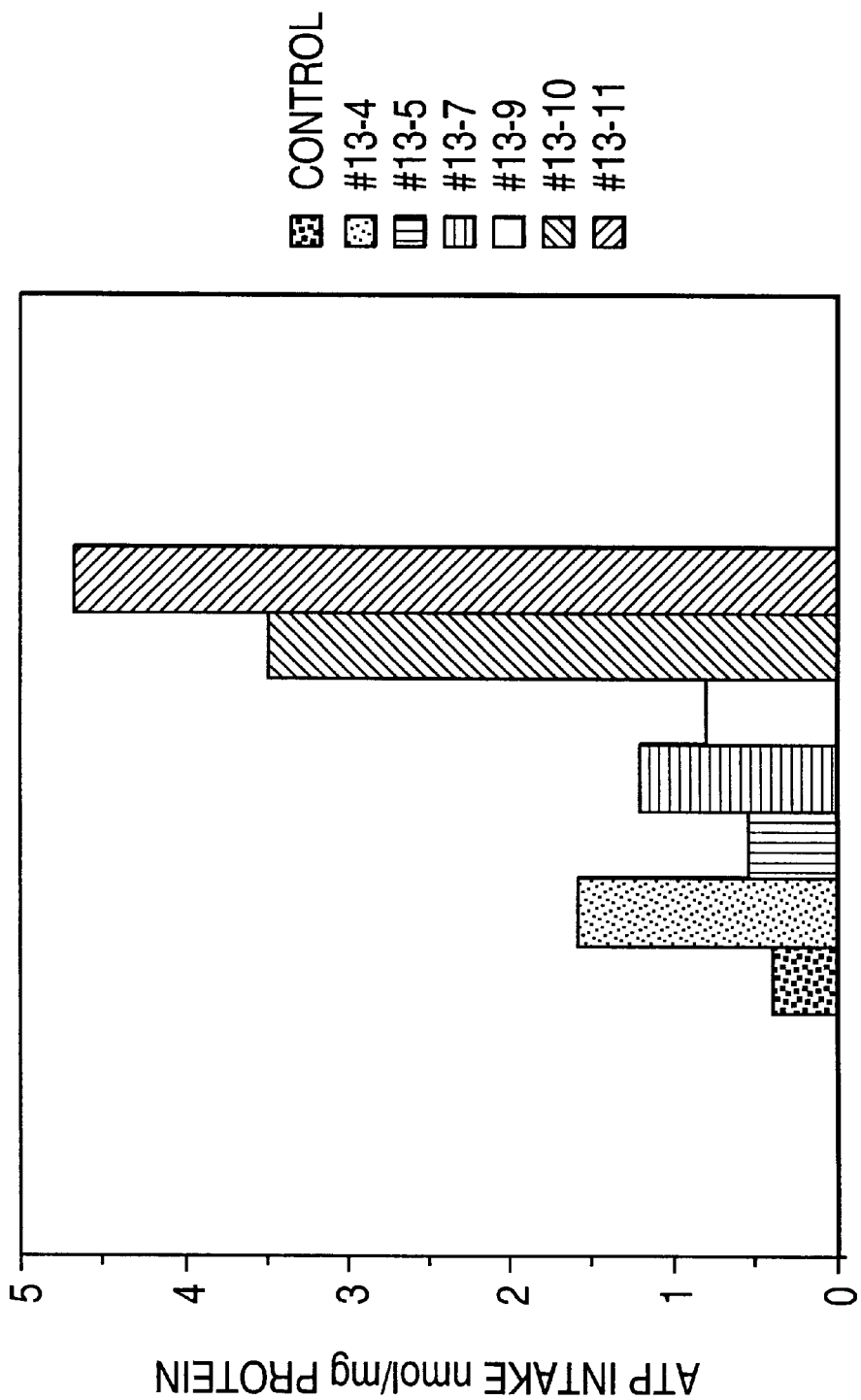

VIRUS RESISTANT PLANTS EXPRESSING ANIMAL CELL-DERIVED (2'-5') OLIGADENYLATE SYNTHETASE AND RIBONUCLEASE L AND A METHOD FOR CREATING THE SAME

TECHNICAL FIELD

The present invention relates to a technology for creating a virus resistant plant expressing an animal cell-derived (2'-5') oligoadenylate synthetase and an animal cell-derived ribonuclease L using recombinant DNA technology. More specifically, the present invention relates to a method for creating a plant having resistance to viruses, comprising incorporating DNA sequences encoding an animal cell-derived (2'-5')oligoadenylate synthetase and an animal cell-derived ribonuclease L into a chromosome(s) of the plant and expressing the DNA sequences; and a virus resistant plant obtained by the above method.

BACKGROUND ART

Viruses are one of the major stress sources for plants. It is not seldom that crop-producing districts shift or cultivars are renewed due to damage from viral diseases. At present, there is no effective drug that acts on viruses directly. Thus, plants infected with viruses are subjected to incineration. Although virus resistance is an important goal for breeding, it has been impossible to rear a virus resistant cultivar with conventional breeding technologies such as crossing where a source of a resistance gene cannot be found in wild-type or related species.

As a method for supplementing such conventional breeding technologies, a method have been developed recently in which virus resistance is conferred on plants using recombinant DNA technology. Recombinant DNA technology has made gene transfer possible which goes beyond the deadlock of conventional crossing described above. Furthermore, this technology allows to introduce into existing cultivars a virus resistance gene alone and, thus, it has become possible to save the time required for breeding greatly.

As a method for creating virus resistant plants using recombinant DNA technology, methods of expressing a gene encoding a virus coat protein or a viral replication protein, an antisense gene, and a gene encoding a satellite RNA, and the like have been reported (see, for example, Arch. Virol., 115, 1, 1990). These methods confer resistance to only one kind of virus or its related viruses alone. A method for conferring resistance to various kinds of viruses is still under development.

As a method for conferring resistance to a large number of viruses at the same time, a method using a double-stranded RNA specific ribonuclease (International Publication WO93/20686) and a method using a (2'-5') oligoadenylate synthetase (Bio/Technology, 11, 1048, 1993) have been reported.

With respect to the method using a (2'-5')oligoadenylate synthetase, it has been reported that the virus resistance in the resultant transformant plants is extremely weak (The Proceedings of XVIIIth Eucarpia Symposium, Section Ornamentals, 1995). Briefly, a (2'-5')oligoadenylate synthetase was introduced into a tobacco plant (cv Samsun) and then the tobacco mosaic virus (hereinafter referred to as "TMV") OM strain was inoculated into the resultant plant expressing the (2'-5')oligoadenylate synthetase. As a result, no delay in the development of disease symptoms was recognized as compared to controls. Also, there have been many reports that the existence of ribonuclease L-like molecules are not recognized in plant cells (Biochem. Biophys. Res. Commun., 108, 1243, 1982; J. Biol. Chem., 259, 3482, 1984; The Proceedings of XVIIIth Eucarpia Symposium, Section Ornamentals, 1995).

DISCLOSURE OF THE INVENTION

The present inventors have made intensive and extensive researches expecting that, by expressing both an animal cell-derived (2'-5')oligoadenylate synthetase gene and an animal cell-derived ribonuclease L gene in a plant, virus resistance will be remarkably increased compared to that obtained by the expression of a (2'-5') oligoadenylate synthetase gene alone. Thus, the present invention has been achieved.

The present invention relates to a method for creating a plant having resistance to RNA viruses, comprising incorporating a DNA sequence encoding an animal cell-derived (2'-5')oligoadenylate synthetase (hereinafter referred to as "2-5Aase") and a DNA sequence encoding an animal cell-derived ribonuclease L (hereinafter referred to as "RNaseL") into a chromosome(s) of the plant and expressing the DNA sequences; and a virus resistant plant created by the above method.

Hereinbelow, the present invention will be described in detail.

(1) DNA Sequences Encoding 2-5Aase and RNaseL, Respectively

The presence of a 2-5Aase/RNaseL system in animal cells has been known as partly contributing to the anti-virus state induced by interferon (Annu. Rev. Biochem., 51, 251, 1982). 2-5Aase protein is a protein having an enzymatic activity to synthesize (2'-5') oligoadenylate (usually a trimer or tetramer; hereinafter referred to as "2-5A") from its substrate adenosine triphosphate (ATP) when activated upon recognition of double-stranded RNA. A cDNA encoding 2-5Aase has been cloned from human (EMBO J., 4, 2249, 1985), mouse (J. Biol. Chem., 266, 15293, 1991; Nuc. Acids. Res., 19, 1919, 1991) and rat (EMBL Acc. No. Z18877). This time, the present inventors have succeeded in cloning a cDNA encoding 2-5Aase from bovine. Other DNA sequences encoding 2-5Aase may also be used in the present invention as long as they can provide the above-described 2-5Aase activity. In other words, DNA sequences encoding 2-5Aase cloned from animal species other than those enumerated above, and even the above DNA sequences having replacement, deletion, addition or insertion in the encoded amino acids may also be used in the present invention as long as they can provide the above-described 2-5Aase activity. RNaseL protein is a protein which has an activity to bind with 2-5A and which exhibits RNA degradation activity upon binding with 2-5A. A cDNA encoding RNaseL has been cloned from human (Cell, 72, 753, 1993). Also, the present inventors have succeeded this time in cloning a cDNA encoding RNaseL from bovine. Other DNA sequences encoding RNaseL may also be used in the present invention. DNA sequences encoding RNaseL cloned from animal species other than those mentioned above, and even the above DNA sequences having replacement, deletion, addition or insertion in the encoded amino acids may also be used in the present invention as long as they can provide the above-described RNaseL activity.

In the Examples described below, human- or bovine-derived cDNA clones are used as DNA sequences encoding 2-5Aase and RNaseL. Needless to say, however, DNA sequences encoding 2-5Aase and RNaseL which may be used in the present invention are not limited to these human- or bovine-derived 2-5Aase and RNaseL.

In general, when a DNA sequence is coding for a polypeptide having an amino acid sequence, there exist a plurality of DNA sequences (degenerate isomers) corresponding to the single amino acid sequence because there exist a plurality of genetic codes (codons) corresponding to an amino acid. In the DNA sequences encoding 2-5Aase and RNaseL used in the present invention, it is needless to say that any genetic code may be used as long as it does not alter the amino acid sequence of the polypeptide encoded by the DNA sequence.

(2) Expression of DNA Sequences Encoding 2-5Aase and RNaseL, Respectively

In order for DNA sequences encoding 2-5Aase and RNaseL, respectively, to be expressed in a transgenic plant, at least these DAN sequences must be transcribed into RNAS. When a foreign gene is incorporated in a plant chromosome, it is known that such a gene is incorporated into a transcription region on the chromosome with a certain probability (EMBO J., 6, 3891, 1987). Therefore, it is possible to incorporate a DNA sequence encoding 2-5Aase or RNaseL alone into a plant chromosome and to express it in the plant. However, it is preferable to incorporate such a DNA sequence after ligating thereto appropriate promoter and terminator sequences.

In this case, as a promoter, any promoter which has been known to function in plant cells may be used. Specific examples include a promoter for a gene encoding ribulose-1,5-bisphosphate carboxylase small subunit; a promoter for nopaline synthetase gene; a promoter allowing production of cauliflower mosaic virus 35S-RNA (CaMV 35S promoter) (Proc. Natl. Acad. Sci. USA, 83, 2358, 1986; Plant Cell Rep., 4, 355, 1985; Cell, 30, 763, 1982; Nature, 313, 810, 1985) and the like. As a terminator, any terminator which has been known to function in plant cells may be used. Specific examples include a terminator for nopaline synthetase gene; a terminator for octopine synthetase gene (J. Mol. Appl. Gen., 1, 561, 1982; EMBO J., 3, 835, 1984) and the like.

(3) Incorporation of DNA Sequences Encoding 2-5Aase and RNaseL into a Plant

For the introduction of a DNA sequence encoding 2-5Aase or RNaseL various methods already reported and established may be used. For example, a method using the Ti plasmid of *Agrobacterium tumefaciens* as a vector, a method of introducing a DNA sequence directly into plant sections or plant protoplasts, or the like may be used depending on the plant species of interest (see, for example, "Plant Genetic Transformation and Gene Expression; A Laboratory Manual", Draper, J. et al., Blackwell Scientific Publications, 1988). By tissue culturing the transformed plant tissues or cells under appropriate conditions for the plant species, the transformed plant can be regenerated. As a method for obtaining a transformed plant which expresses 2-5Aase simultaneously with RNaseL, a method may be considered which comprises examining the expression of each of the genes of interest in 2-5Aase-introduced plant and RNaseL-introduced plant and crossing a plant expressing 2-5Aase with a plant expressing RNaseL. Alternatively, a 2-5Aase- or RNaseL-introduced transformant plant may be re-transformed with RNaseL gene or 2-5Aase gene, respectively. It is also possible to transform a plant with both 2-5Aase gene and RNaseL gene at the same time.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 is a diagram showing vectors for plant transformation which individually comprise a human-derived 2-5Aase cDNA or a human-derived RNaseL cDNA, respectively.

NOSpro: nopaline synthetase gene promoter
NOSterm: nopaline synthetase gene terminator
CaMV35S: cauliflower mosaic virus 35S promoter
NPTII: neomycin resistance gene
HYG: hygromycin resistance gene
2-5Aase: 2-5Aase cDNA
RNaseL(T): partial length RNaseL CDNA
RNaseL(F): full length RNaseL cDNA
RB: right border
LB: left border FIG. 2 is a graph showing the activity of 2-5Aase in leaves of a 2-5Aase-introduced transformant tobacco plant (cv Xanthi nc).

Control: non-transformant
2-5Aase#11b: transformant
2-5Aase#12a: transformant
2-5Aase#13b: transformant

Control: non-transformant
RNaseL#H1: transformant
RNaseL#H2: transformant
RNaseL#H3: transformant
RNaseL#H4: transformant
Spleen: crude extract from mouse spleen

Control: non-transformant
RNaseL(F)#23a: transformant
RNaseL(F)#14a: transformant
RNaseL(F)#27a: transformant
RNaseL(F)#12b: transformant
RNaseL(F)#30b: transformant
Spleen: crude extract from mouse spleen

2-5Aase#11b: 2-5Aase-introduced tobacco
2-5Aase#11b+RNaseL#H4: [2-5Aase+partial length RNaseL]-introduced tobacco FIGS. 7A and 7B show photographs of plant morphologies exhibiting the presence or absence of necrotic spots in 2-5Aase+RNaseL (F)-introduced tobacco, 2-5Aase-introduced tobacco and RNaseL (F)-introduced tobacco 3 days after inoculation with CMV Y strain.

A. 2-5Aase#13b
B. 2-5Aase#13b+RNaseL(F)#23a
C. RNaseL(F) #23a
D. 2-5Aase#13b

E. 2-5Aase#13b+RNaseL(F)#27a

F. RNaseL(F)#27a

G. 2-5Aase#13b

H. 2-5Aase#13b+RNaseL(F)#30b

I. RNaseL(F)#30b

↑ Inoculated leaves

Figure 8B:
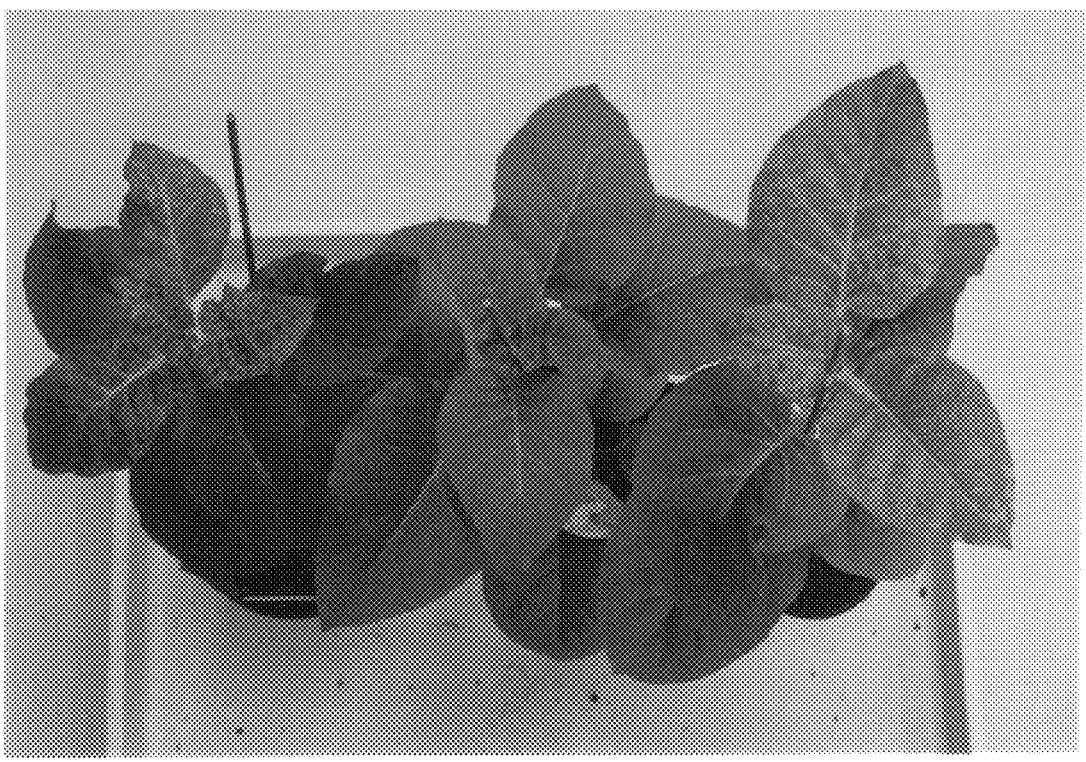

FIGS. 8A and 8B show photographs of plant morphologies exhibiting the presence or absence of systemic symptoms in 2-5Aase+RNaseL(F)-introduced tobacco, 2-5Aase-introduced tobacco and RNaseL(F)-introduced tobacco 12 days after inoculation with CMV Y strain.

A. 2-5Aase#13b

B. 2-5Aase#13b+RNaseL(F)#23a

C. RNaseL(F)#23a

D. 2-5Aase#13b

E. 2-5Aase#13b+RNaseL(F)#27a

F. RNaseL(F)#27a

G. 2-5Aase#13b

H. 2-5Aase#13b+RNaseL(F)#30b

I. RNaseL(F)#30b

Figure 9:
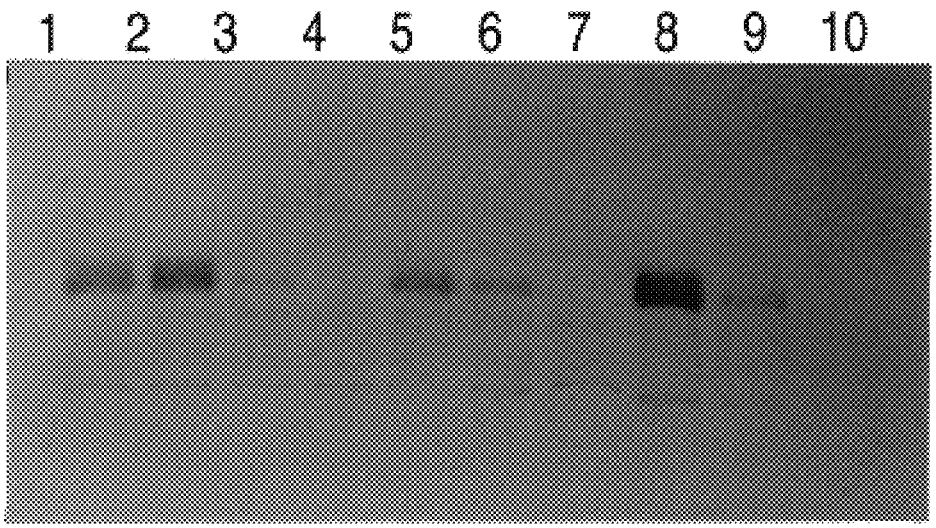

FIG. 9 is a photograph showing the results of electrophoresis to detect CMV in portions with no necrotic spots in inoculated leaves exhibiting necrotic spots in various transformant tobacco plants 5 days after inoculation.

Figure 10:
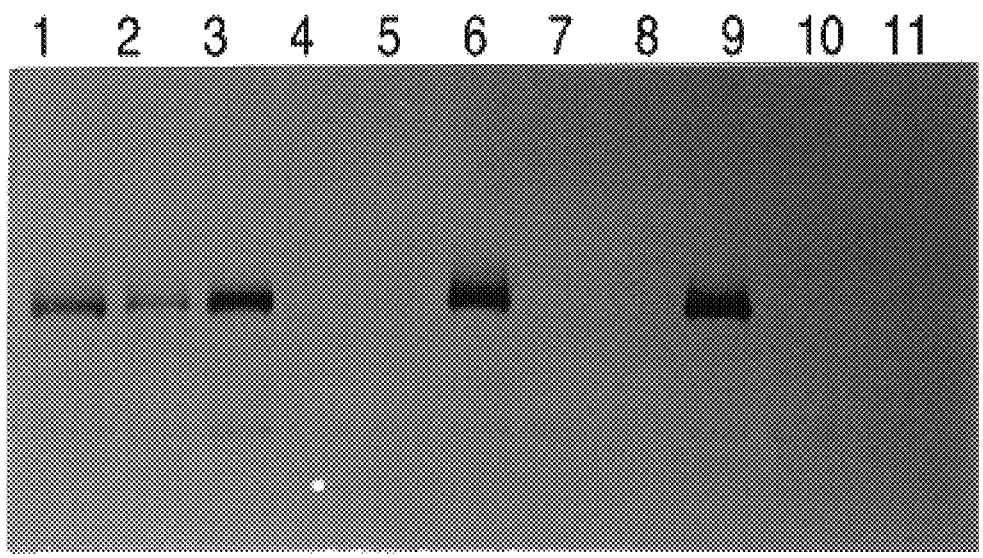

1. 2-5Aase#13b
2. RNaseL(F)#23a
3. 2-5Aase#13b+RNaseL(F)#23a: portion with necrotic spot formation
4. 2-5Aase#13b+RNaseL(F)#23a: portion without necrotic spots
5. RNaseL(F)#30b
6. 2-5Aase#13b+RNaseL(F)#30b: portion with necrotic spot formation
7. 2-5Aase#13b+RNaseL(F)#30b: portion without necrotic spots
8. RNaseL(F)#27a
9. 2-5Aase#13b+RNaseL(F)#27a: portion with necrotic spot formation
10. 2-5Aase#13b+RNaseL(F)#27a: portion without necrotic spots FIG. 10 is a photograph showing the results of electrophoresis to detect CMV in uninoculated upper leaves in various transformant tobacco plants 12 days after inoculation.

1. Non-transformant
2. 2-5Aase#13b
3. RNaseL(F)#23a
4, 5 2-5Aase#13b+RNaseL(F)#23a
6 RNaseL(F)#27a
7, 8 2-5Aase#13b+RNaseL(F)#27a
9 RNaseL(F)#30b
10, 11 2-5Aase#13b+RNaseL(F)#30b FIG. 11 shows photographs of plant morphologies exhibiting the presence or absence of necrotic spots in 2-5Aase+RNaseL (F)-introduced tobacco, 2-5Aase-introduced tobacco and RNaseL (F)-introduced tobacco 5 days after inoculation with a crude extract from CMV Y strain-infected leaves.

A. 2-5Aase#13b

B. 2-5Aase#13b+RNaseL(F)#23a

C. RNaseL(F)#23a

D. 2-5Aase#13b

E. 2-5Aase#13b+RNaseL(F)#30b

F. RNaseL(F)#30b

↑ Inoculated leaves

FIG. 12 shows photographs of plant morphologies exhibiting the presence or absence of systemic symptoms in 2-5Aase+RNaseL (F)-introduced tobacco, 2-5Aase-introduced tobacco and RNaseL (F)-introduced tobacco 16 days after inoculation with a crude extract from CMV Y strain-infected leaves.

A. 2-5Aase#13b

B. 2-5Aase#13b+RNaseL(F)#23a

C. RNaseL(F)#23a

D. 2-5Aase#13b

E. 2-5Aase#13b+RNaseL(F)#30b

F. RNaseL(F)#30b

FIG. 13 shows photographs of plant morphologies exhibiting the presence or absence of necrotic spots in 2-5Aase+RNaseL (F)-introduced tobacco, 2-5Aase-introduced tobacco and RNaseL (F)-introduced tobacco 5 days after inoculation with a crude extract from PVY T strain-infected leaves.

A. 2-5Aase#13b

B. 2-5Aase#13b+RNaseL(F)#23a

C. RNaseL (F) #23a

D. 2-5Aase#13b

E. 2-5Aase#13b+RNaseL(F)#30b

F. RNaseL(F)#30b

↑ Inoculated leaves

Figure 14B:
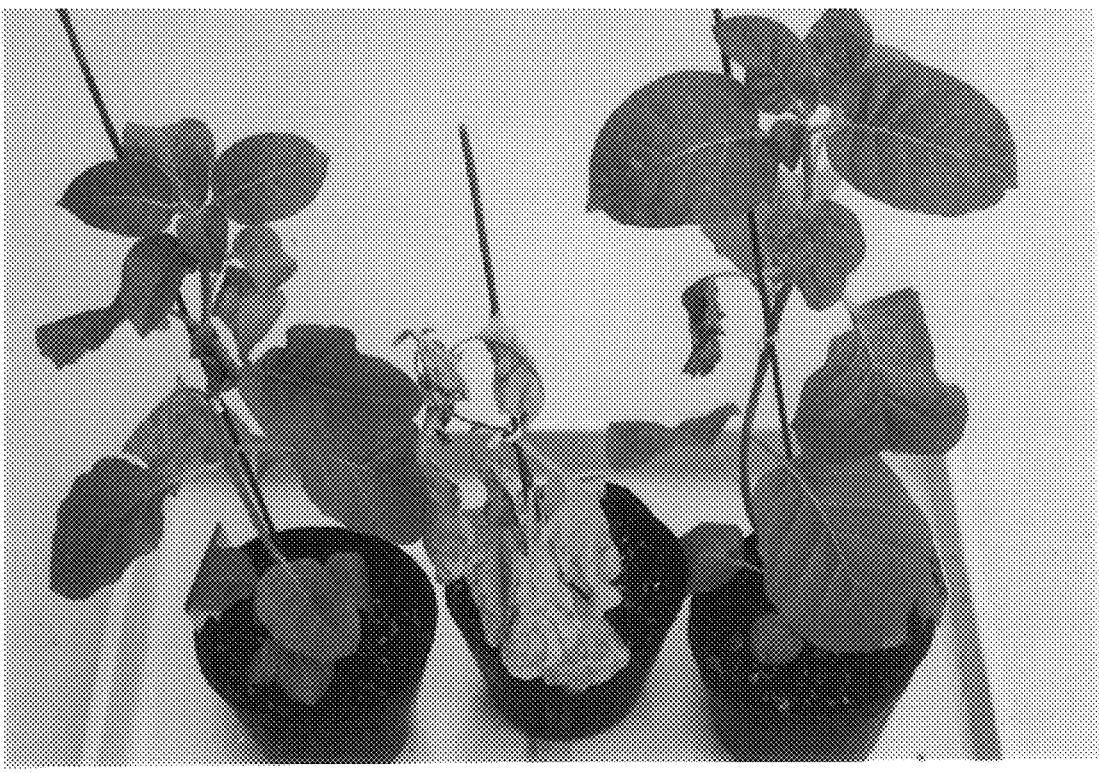

FIGS. 14A and 14B show photographs of plant morphologies exhibiting the presence or absence of systemic symptoms in 2-5Aase+RNaseL(F)-introduced tobacco, 2-5Aase-introduced tobacco and RNaseL(F)-introduced tobacco 14 days after inoculation with a crude extract from PVY T strain-infected leaves.

A. 2-5Aase#13b

B. 2-5Aase#13b+RNaseL(F)#23a

C. RNaseL(F)#23a

D. 2-5Aase#13b

E. 2-5Aase#13b+RNaseL(F)#27a

F. RNaseL(F)#27a

G. 2-5Aase#13b

H. 2-5Aase#13b+RNaseL(F)#30b

I. RNaseL(F)#30b

Figure 15A:
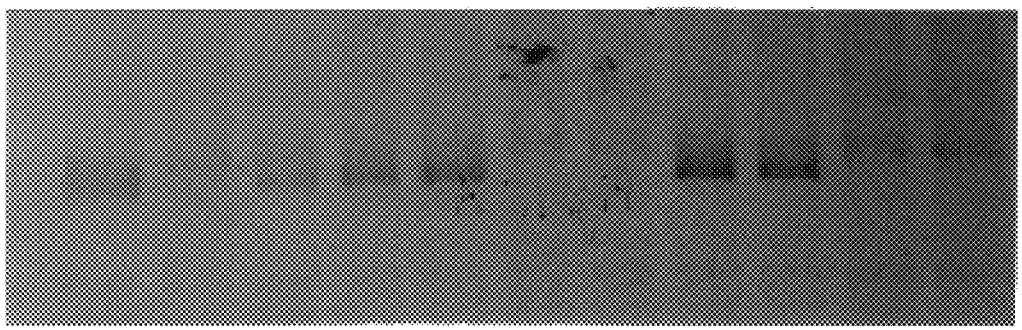
Figure 15B:
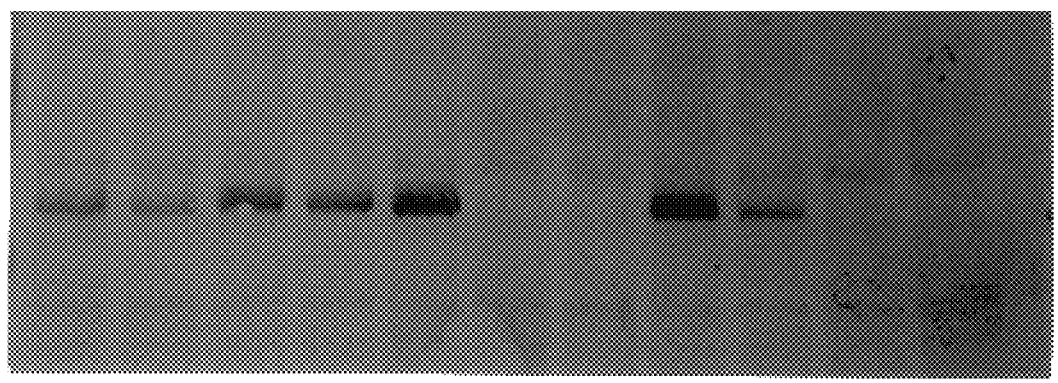

FIG. 15 shows photographs representing the results of electrophoresis to detect PVY T strain in uninoculated upper leaves 5 days after infection (A) and uninoculated upper leaves 10 days after infection (B) in various transformant tobacco plants.

Figure 16B:
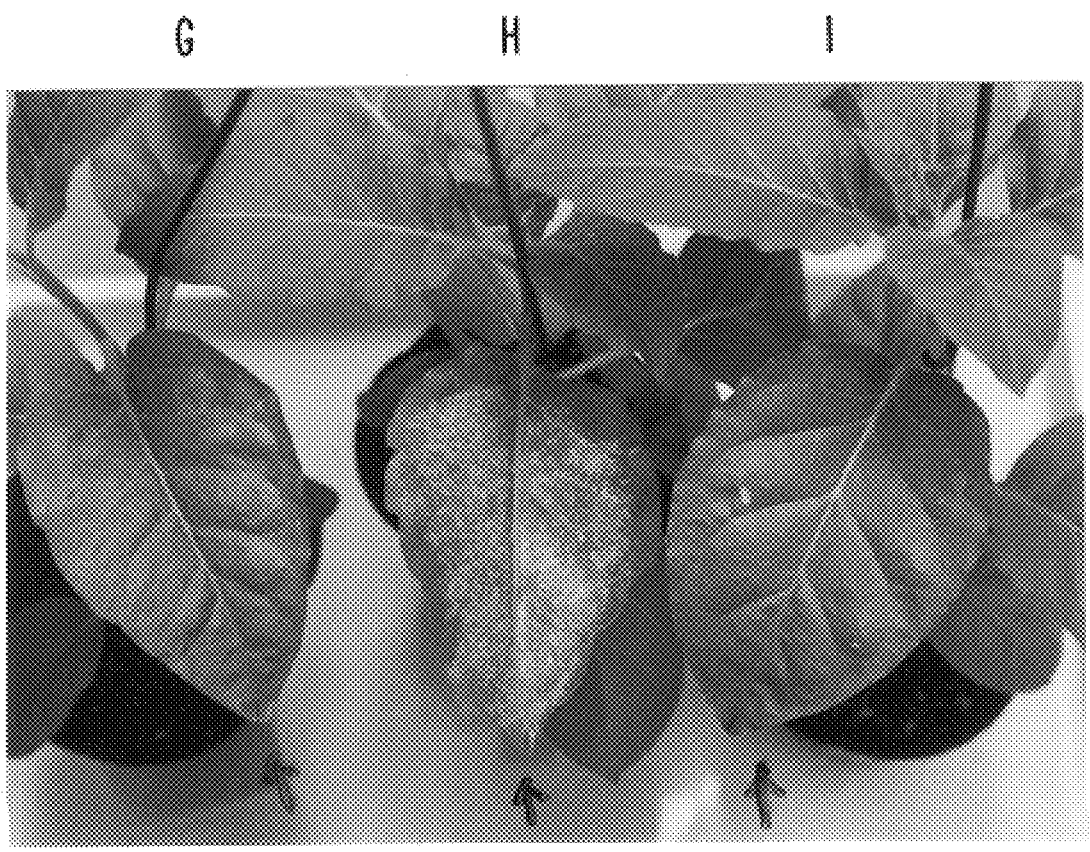

1. Non-transformant
2, 3 2-5Aase#13b
4, 5 RNaseL(F)#23a
6, 7 2-5Aase#13b+RNaseL(F)#23a
8, 9 RNaseL(F)#30b
10,11 2-5Aase#13b+RNaseL(F)#30b FIGS. 16A and 16B show photographs of plant morphologies exhibiting the presence or absence of necrotic spots in 2-5Aase+RNaseL(F)-introduced tobacco, 2-5Aase-introduced tobacco and RNaseL(F)-introduced tobacco 3 days after inoculation with a crude extract from PVY O strain-infected leaves.

Figure 17B:

A. 2-5Aase#13b
B. 2-5Aase#13b+RNaseL(F)#23a
C. RNaseL(F)#23a
D. 2-5Aase#13b
E. 2-5Aase#13b+RNaseL(F)#27a
F. RNaseL(F)#27a
G. 2-5Aase#13b
H. 2-5Aase#13b+RNaseL(F)#30b
I. RNaseL(F)#30b
↑ Inoculated leaves FIGS. 17A and 17B show photographs of plant morphologies exhibiting the presence or absence of systemic symptoms in 2-5Aase+RNaseL(F)-introduced tobacco, 2-5Aase-introduced tobacco and RNaseL(F)-introduced tobacco 15 days after inoculation with a crude extract from PVY O strain-infected leaves.

Figure 18A:
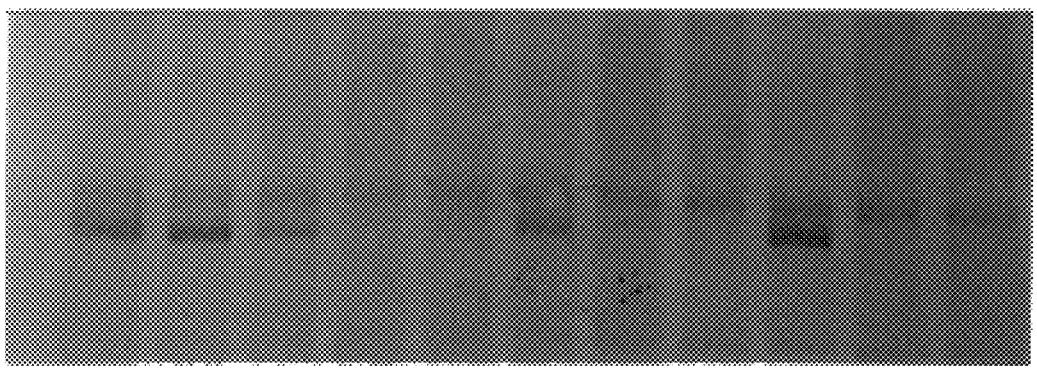
Figure 18B:
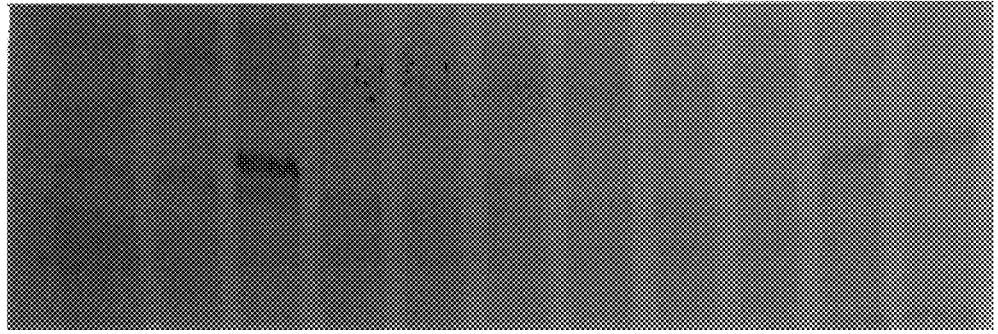

A. 2-5Aase#13b
B. 2-5Aase#13b+RNaseL(F)#23a
C. RNaseL(F)#23a
D. 2-5Aase#13b
E. 2-5Aase#13b+RNaseL(F)#27a
F. RNaseL(F)#27a
G. 2-5Aase#13b
H. 2-5Aase#13b+RNaseL(F)#30b
I. RNaseL(F)#30b FIG. 18 shows photographs representing the results of electrophoresis to detect PVY O strain in inoculated leaves 5 days after inoculation (A) and uninoculated upper leaves 6 days after inoculation (B) in various transformant tobacco plants.

1. Non-transformant
2. 2-5Aase#13b
3. RNaseL(F)#23a
4, 5 2-5Aase#13b+RNaseL(F)#23a
6 RNaseL(F)#27a
7, 8 2-5Aase#13b+RNaseL(F)#27a
9. RNaseL(F)#30b
10, 11 2-5Aase#13b+RNaseL(F)#30b FIGS. 19A through 19D show the base sequence of SEQ ID NO: 9 for a bovine 2-5Aase cDNA and an amino acid sequence deduced therefrom.

FIGS. 20A through 20F show the base sequence of SEQ ID NO: 10 for a bovine RNaseL cDNA and an amino acid sequence deduced therefrom.

FIG. 21 is a graph showing the activity of 2-5Aase in leaves of 2-5Aase-introduced transformant tobacco (cv Samsun).

Figure 22:
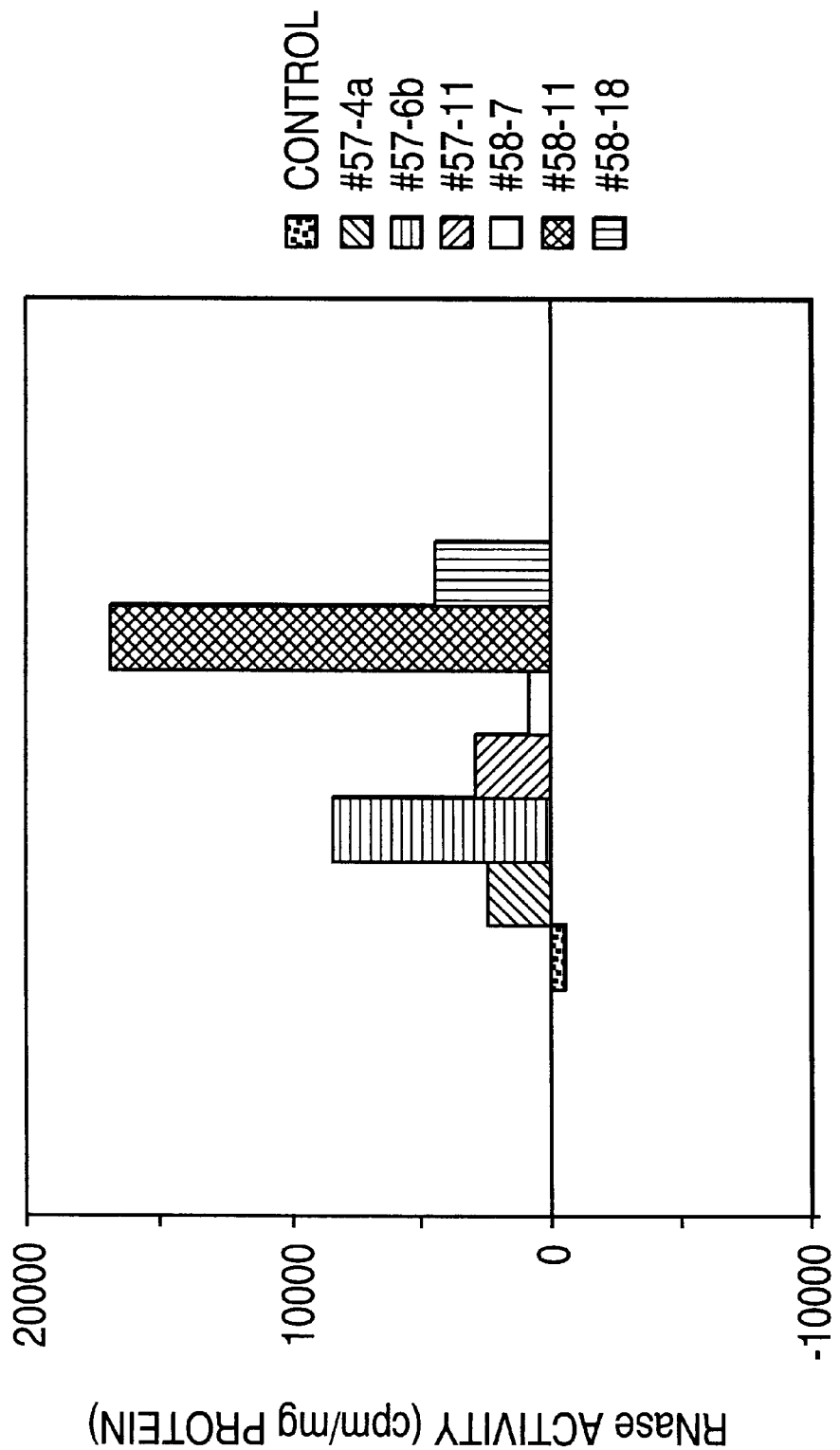

Control: Non-transformant
13-4: 2-5Aase-introduced transformant
13-5: 2-5Aase-introduced transformant
13-7: 2-5Aase-introduced transformant
13-9: 2-5Aase-introduced transformant
13-10: 2-5Aase-introduced transformant
13-11: 2-5Aase-introduced transformant FIG. 22 is a graph showing the activity of RNaseL in leaves of RNaseL (F)-introduced transformant tobacco (cv Samsun).

Figure 23:
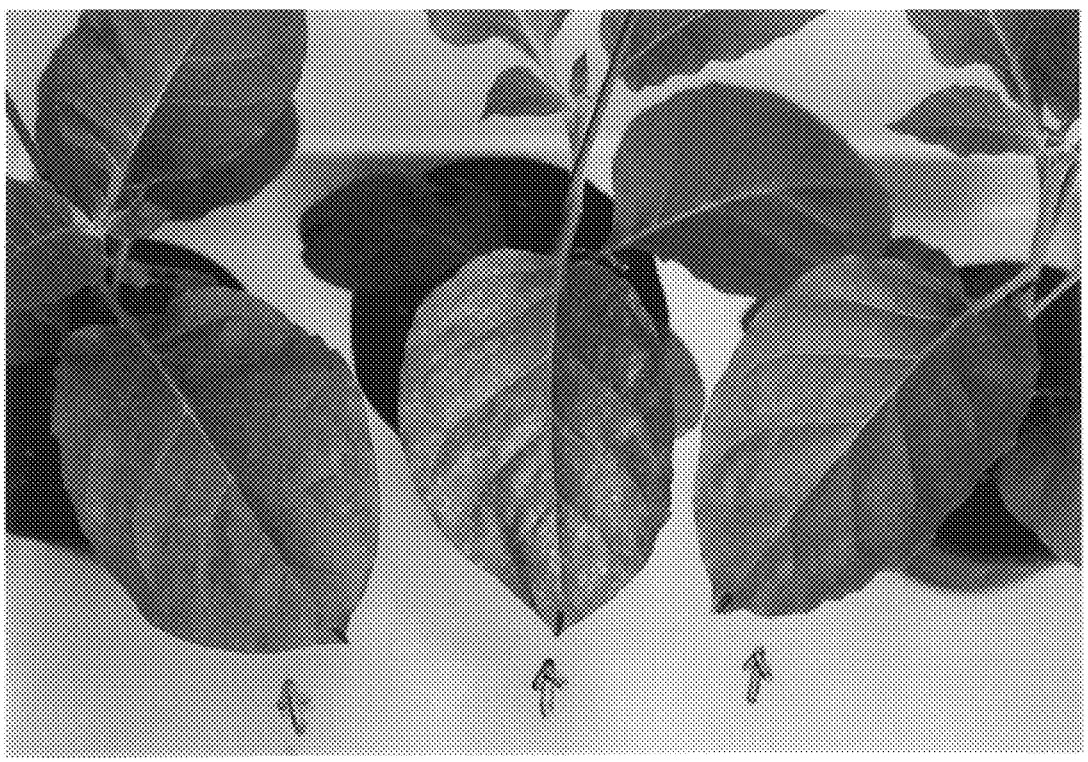

Control: Non-transformant
57-4a: RNaseL(F)-introduced transformant
57-6b: RNaseL(F)-introduced transformant
57-11: RNaseL(F)-introduced transformant
58-7: RNaseL(F)-introduced transformant
58-11: RNaseL(F)-introduced transformant
58-18: RNaseL(F)-introduced transformant FIG. 23 shows photographs of plant morphologies exhibiting the presence or absence of necrotic spots in 2-5Aase+RNaseL(F)-introduced tobacco, 2-5Aase-introduced tobacco and RNaseL(F)-introduced tobacco 3 days after inoculation with a crude extract from CMV Y strain-infected leaves.

Figure 24:
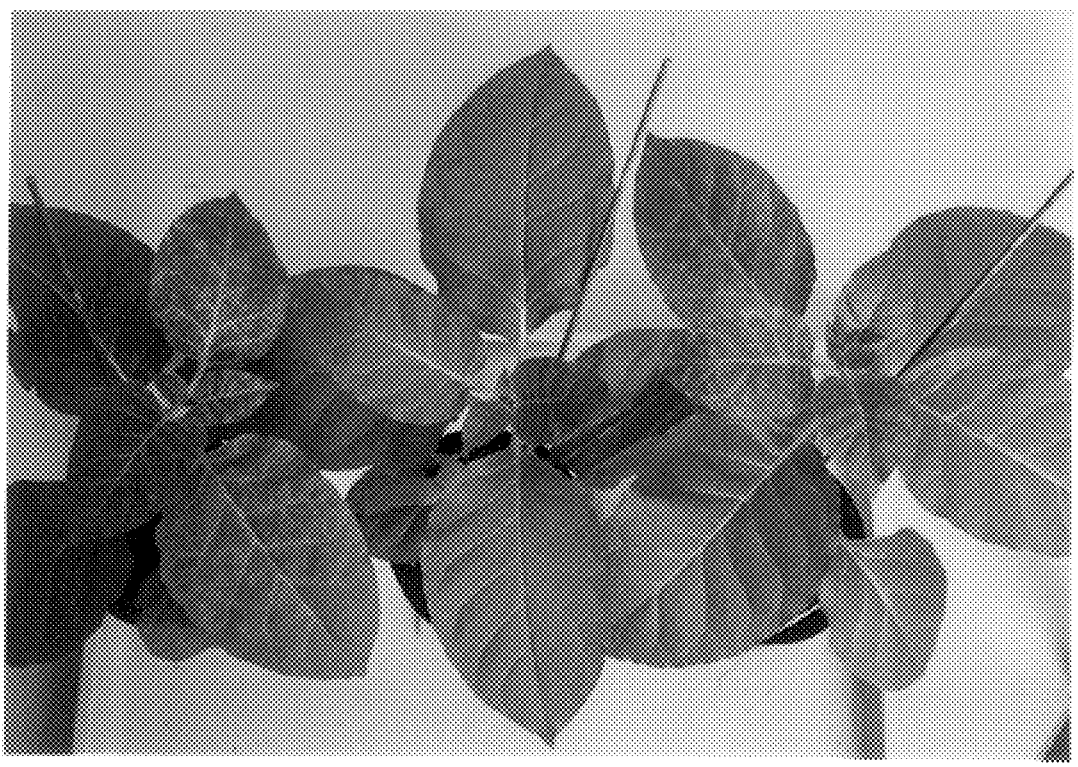

A. 2-5Aase(S)#13-10
B. 2-5Aase(S)#13-10+RNaseL(S)#57-6b
C. RNaseL(S)#57-6b
↑ Inoculated leaves FIG. 24 shows photographs of plant morphologies exhibiting the presence or absence of systemic symptoms in 2-5Aase+RNaseL(F)-introduced tobacco, 2-5Aase-introduced tobacco and RNaseL(F)-introduced tobacco 10 days after inoculation with a crude extract from CMV Y strain-infected leaves.

A. 2-5Aase(S)#13-10
B. 2-5Aase(S)#13-10+RNaseL(S)#57-6b
C. RNaseL(S)#57-6b

BEST MODE FOR CARRYING OUT THE INVENTION

Hereinbelow, the present invention will be described in more detail with reference to the following Examples, which should not be construed as limiting the present invention.

In the following Examples, human-derived cDNAs were used as DNA sequences for 2-5Aase and RNaseL, and CaMV 35S promoter was used as a promoter for expressing the above genes in plants. For the expression of the 2-5Aase cDNA, pBI121 vector (EMBO J., 6, 3901, 1987) was used after replacing its β-glucuronidase gene (β GUS) with the 2-5Aase cDNA. For the expression of the RNaseL cDNA, PBIB-HYG vector (obtained from Dr. Detlef Becker, Institute for Genetics, Cologne University) was used after introducing thereinto a DNA sequence obtained by ligating CaMV 35S promoter upstream of the 5' end to RNaseL cDNA.

As a host plant to confirm the effect of the present invention, a tobacco cultivar (Xanthi nc) was used. By the Agrobacterium-mediated leaf disk method or electroporation using tobacco protoplasts, tobacco transformants were obtained from the above strain ("Plant Genetic Transformation and Gene Expression; A Laboratory Manual", Draper, J. et al., Blackwell Scientific Publications, 1988).

The presence or absence of expression of the 2-5Aase or RNaseL cDNA in the transformants was examined by preparing crude extracts from transformant leaves and determining the 2-5Aase activity (J. Biol. Chem., 259, 1363, 1984) and the RNaseL activity (Anal. Biochem., 144, 450, 1985) separately.

A transformant tobacco expressing both the 2-5Aase cDNA and the RNaseL cDNA was obtained by crossing a tobacco plant expressing the 2-5Aase activity with a tobacco plant expressing the RNaseL activity. When a tobacco plant expressing 2-5Aase alone and a tobacco plant expressing both 2-5Aase and RNaseL were inoculated with cucumber mosaic virus (CMV Y strain), the latter plant exhibited a significantly higher virus resistance than the former plant.

EXAMPLE 1

Construction of Plasmids for Use in Creating Transformant Plants (FIG. 1)

Based on the DNA sequence (SEQ ID NO: 1) for the human-derived 2-5Aase described in Proc. Natl. Acad. Sci.

USA, 80, 4904, 1983, a probe for CDNA cloning (SEQ ID NO: 2) was prepared. A library for cDNA cloning was prepared by treating HeLa cells (obtained from Assistant Professor Enomoto, Division of Physiochemistry, Department of Pharmacology, the University of Tokyo) with 200 units/ml of human β interferon (Paesel Lorei GMBH & CO., Frankfurt) for 12 hours, extracting mRNAs therefrom, preparing cDNAs from the mRNA using a Pharmacia CDNA synthesis kit, and ligating the cDNAs to Lambda gt10 vector. It has been reported that there are two 2-5Aase mRNAs (1.6 kb and 1.8 kb). For expression in plants, the cDNA corresponding to the 1.6 kb mRNA was used. A plasmid pBI2-5Aase for expression in plant was prepared by replacing β GUS in pBI121 with the 2-5Aase cDNA (EcORI fragment).

The human-derived RNaseL cDNA was obtained by preparing a probe (SEQ ID NO: 4) based on the DNA sequence (SEQ ID NO: 3) disclosed in Cell, 72, 753, 1993 and screening a human spleen cDNA library (Clontech) with the probe. From the human spleen cDNA library, two cDNA clones were obtained: a partial length clone (lacking C-terminal 61 amino acid residues) and a full length clone. To the N-terminal of each of these two RNaseL cDNAs (HindIII-EcoRI fragments), CaMV 35S promoter was ligated and then the resultant fragment was replaced with the HindIII-SacI fragment of PBIB-HYG vector, to thereby obtain plasmids for expression in plant. The plasmid containing the partial length RNaseL and the plasmid containing the full length RNaseL are designated pBIBRNaseL(T) and pBIBRNaseL(F), respectively.

EXAMPLE 2

Transformation of Tobacco Plants

Tobacco (*Nicotiana tabacum*) cv Xanthi nc was used for transformation. Plasmids pBI2-5Aase and pBIBRNaseL(F) shown in FIG. 1 were separately introduced into *Agrobacterium tumefaciens* LBA4404 strain by electroporation. Tobacco leaf sections were infected with the Agrobacterium by the leaf disk method and placed on MS-B5 medium [vitamin B5-added Murashige & Skoog basal medium (Physiol. Plant., 15, 473, 1962)] containing 250 μg/ml claforan, 100 μg/ml kanamycin or 20 μg/ml hygromycin to select transformants. When shoots appeared, plants were transferred to hormone-free MS medium to induce rooting. The resultant transformant plants were aseptically cultured in vitro in plant boxes. Then, after potting, they were self-pollinated or crossed (2-5Aase+RNaseL) to obtain R1 seeds.

Plasmid pBIBRNaseL(T) was introduced into protoplasts prepared from tobacco leaves by electroporation. Protoplasts were prepared from tobacco (cv Xanthi nc) mesophyll cells by treating them in an enzyme solution [1% Cellulase Onozuka RS (Yakult), 1% Driselase (Kyowa Hakko Kogyo), 0.1% Pectolyase (Seishin Pharmaceutical), 0.4 M D-mannitol (pH 5.7)] overnight at room temperature. The protoplasts were washed 3 times with cold 0.4 M D-mannitol, and $1 \times 10^8$ protoplasts were suspended in 0.8 ml of an electroporation buffer (0.3 M D-mannitol, 5 mM 2-(N-morpholino)ethanesulfonic acid, pH 5.8, 70 mM KC1) containing about 10 g g of the DNA plasmid. Then, the suspension was transferred into an electroporation cuvette (Bio-Rad, 0.4 cm in width), and a voltage of 300 V was applied at a capacitance of 125μF. The electroporated protoplasts were cultured in 1% agarose-containing spheroplast medium (Murashige & Skoog medium containing 1% sucrose, 0.4 M D-mannitol, 0.2 μg/ml 2,4-dichlorophenoxyacetic acid) for one week at 28° C. under dark conditions. Subsequently, selection of transformants was performed with hygromycin (20 μg/ml). When shoots were formed in the resultant colonies, the colonies were transferred to a hormone-free medium to obtain transformant plants. The resultant transformant plants were aseptically cultured in vitro in plant boxes. Then, after potting, they were crossed with 2-5Aase-introduced plants to obtain F1 seeds.

EXAMPLE 3

Detection of 2-5Aase Activity in 2-5Aase-Introduced Transformant Tobacco (FIG. 2)

A crude extract was prepared from in vitro cultured tobacco leaves and interferon-treated HeLa cells separately by the method of Wells et al. (J. Biol. Chem., 259, 1363, 1984). After measurement of wet weight, leaves were crushed in liquid nitrogen. Then, an equal volume of a lysis buffer [0.5% Nonidet P-40, 90 mM KCl, 1 mM magnesium acetate, 10 mM Hepes, pH 7.6, 2 mM 2-mercaptoethanol, 20 μg/ml leupeptin, 50μg/ml bovine lung aprotinin, 50μM phenylmethyl-sulfonyl fluoride (PMSF), 50 μg/ml trypsin inhibitor] was added thereto, homogenized in a Teflon Pestle homogenizer and centrifuged at 15,000 rpm at 4° C. for 20 minutes twice to obtain the supernatant. To 1 ml of the thus obtained leaf crude extract (in the case of a crude extract from HeLa cells, the extract was diluted 10-fold with the lysis buffer), 40 μl of polyI:polyC cellulose suspension was added and reacted at 4° C. for 2 hours. Then, the reaction solution was washed 3 times by centrifugation with a washing buffer (20 mM Hepes, pH 7.0, 10 mM magnesium acetate, 5 mM KCl), suspended in 50 μl of a reaction mixture (20 mM Hepes, pH 7.0, 20% glycerol, 7 mM 2-mercaptoethanol, 2 mM ATP, 5 mM KCl, 10 mM magnesium acetate) containing 0.2 μl of $^{32}$P-rATP (10 mCi/ml, 3000 Ci/mmol; NEN) and reacted at 30° C. overnight (for 16–20 hours). The $^{32}$P-labelled oligoadenylate produced in the reaction solution was purified by the method of Wells et al. (J. Biol. Chem., 259, 1363, 1984) using DEAE cellulose. Then, the radioactivity was measured with a liquid scintillation counter. The polyI:polyC cellulose was prepared by the method of Wells et al. (J. Biol. Chem., 259, 1363, 1984). The amount of protein in the crude extract was determined with a protein assay kit from Bio-Rad.

2-5Aase-introduced transformants exhibited significantly higher activity than that of non-transformant. In the crude extract from interferon-treated HeLa cells, the amount of ATP intake was 219 nmol/mg protein/4 hours, showing much higher 2-5Aase activity than that in 2-5Aase-introduced tobacco plants.

EXAMPLE 4

Figure 3:
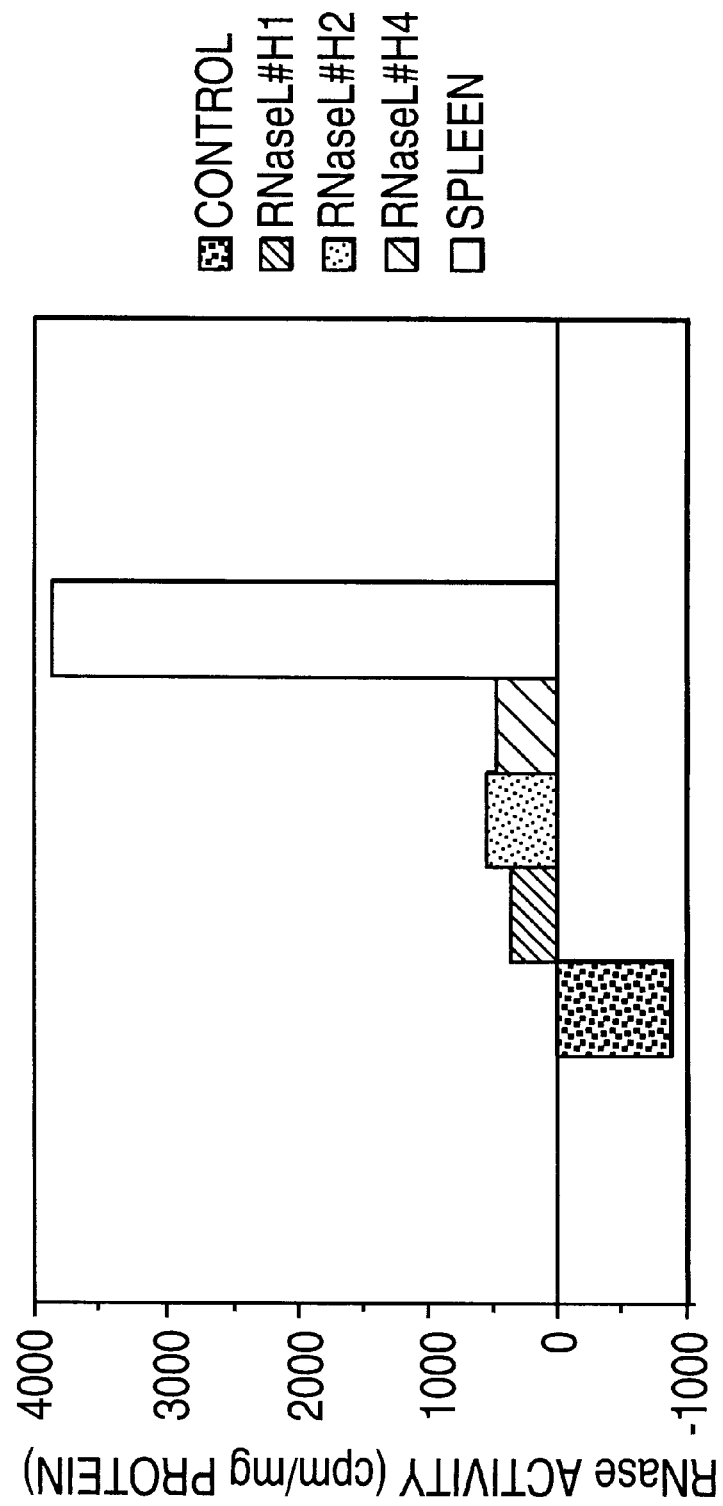
FIG. 3 is a graph showing the activity of RNaseL in leaves of a partial length RNaseL-introduced transformant tobacco plant (cv Xanthi nc).
Figure 4:
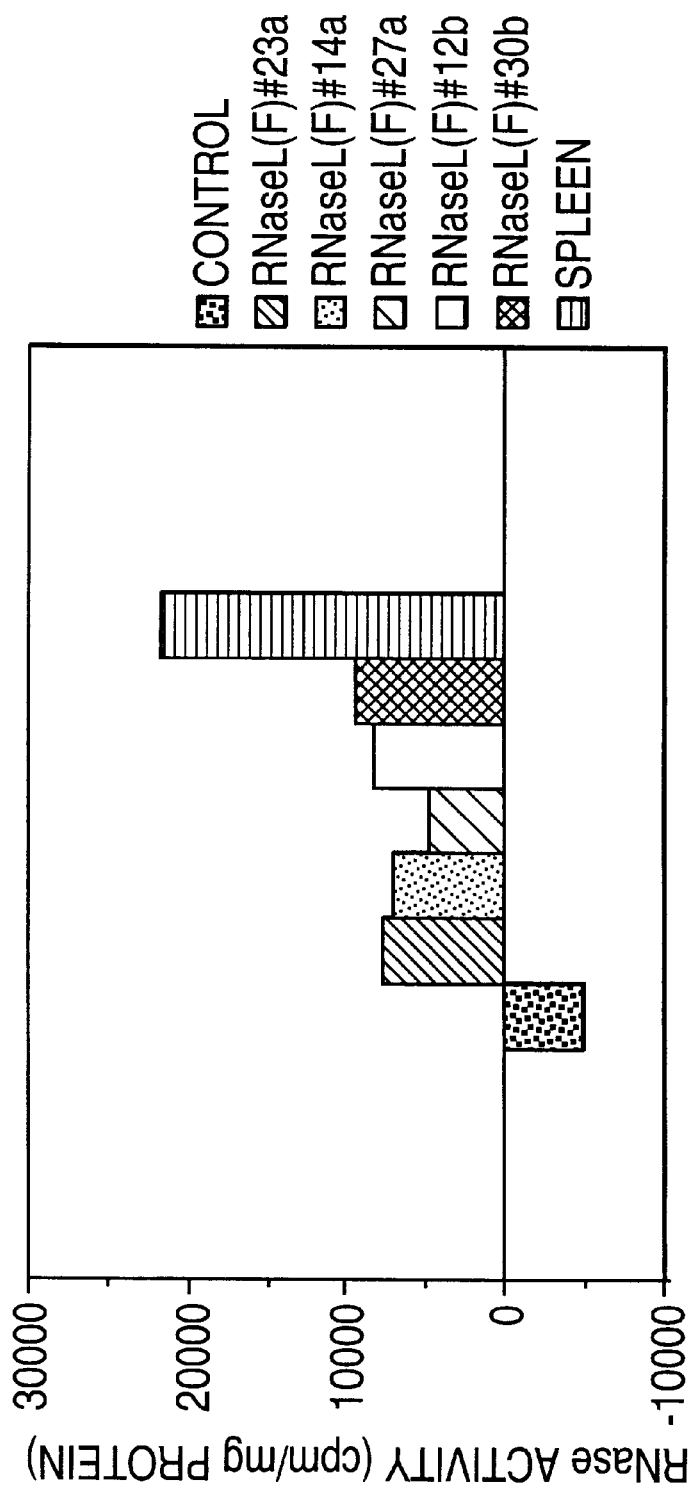
FIG. 4 is a graph showing the activity of RNaseL in leaves of a full length RNaseL-introduced transformant tobacco plant (cv Xanthi nc).

Detection of RNaseL Activity in RNaseL-Introduced Transformant Tobacco (FIGS. 3 and 4)

A crude extract was prepared from in vitro cultured tobacco leaves and mouse spleens separately by the method of Silverman et al. (J. Biol. Chem., 263, 7336, 1988). After measurement of wet weight, leaves were crushed in liquid nitrogen. Then, an equal volume of a hypo buffer (0.5% Nonidet P-40, 20 mM Hepes, pH 7.6, 10 mM potassium acetate, 15 mM magnesium acetate, 1 mM dithiothreitol (DTT), 100μM PMSF, 20μg/ml leupeptin) was added thereto and homogenized with Polytron™. The homogenate was centrifuged twice at 15,000 rpm at 4° C. for 20 minutes and the supernatant was collected to obtain a crude extract. 2-5A (5'-triphosphate tetramer; Seikagaku Kogyo) cellulose and control (ATP) cellulose were prepared in substantially the same manner as described in Example 3 for polyI:polyC cellulose. To 1.0 ml of a tobacco leaf extract (0.5 ml in the case of full length RNaseL-introduced tobacco) or a mouse spleen extract (diluted 4-fold with the hypo buffer), 2.5 µl of 0.1 M ATP and 7.5 µl of 3 M KCl were added and mixed with 25 µl of ATP cellulose suspension. The mixture was reacted at 4° C. for 1 hour and then centrifuged to collect the supernatant. To the supernatant, 25 µl of 2-5Aase cellulose suspension was added and reacted at 4° C. for 2 hours. Then, the supernatant was discarded. The ATP cellulose and 2-5Aase cellulose centrifuged and precipitated after reaction were separately washed 3 times by centrifugation with buffer A (11.5 mM Hepes, pH 7.6, 104 mM KCl, 5.8 mM magnesium acetate, 8.8 mM 2-mercaptoethanol, 10 µM PMSF, 20 µg/ml leupeptin) and suspended in 50 µl of buffer A. A $^{32}$p-labelled polyU substrate was prepared by the method of Silverman (Anal. Biochem., 144, 450, 1985). 20 µl of the above suspension and 20 µl of a reaction solution (4 µl of 100 µM 2-5A, 2 µl of 5×buffer A, 0.25 µl of $^{32}$P-polyUpCp, 0.05 µl of 10 µM cold polyu, 13.7 µl of water) were mixed and reacted at 37° C. overnight (for 16 hours). Then, the reaction was terminated by adding 50 µl of 10 mg/ml yeast RNA and 1 ml of trichloroacetic acid (TCA). The reaction solution was left on ice for more than 15 minutes. Thereafter, the TCA-insoluble fraction was trapped on Whatman GF/C filter and the radioactivity thereof was measured with a liquid scintillation counter. 2-5A dependent RNase activity (i.e., RNaseL activity) was expressed as a difference obtained by subtracting the radioactivity of 2-5A cellulose fraction from the radioactivity of ATP cellulose fraction. The amount of protein in the crude extract was determined with a protein assay kit from Bio-Rad. While the non-transformant tobacco exhibited an activity value below 0 (zero), partial length RNaseL-introduced transformants exhibited positive values (FIG. 3). Full length RNaseL-introduced transformants exhibited still higher activity than that of partial length RNaseL-introduced transformants (FIG. 4).

EXAMPLE 5

Figure 5:
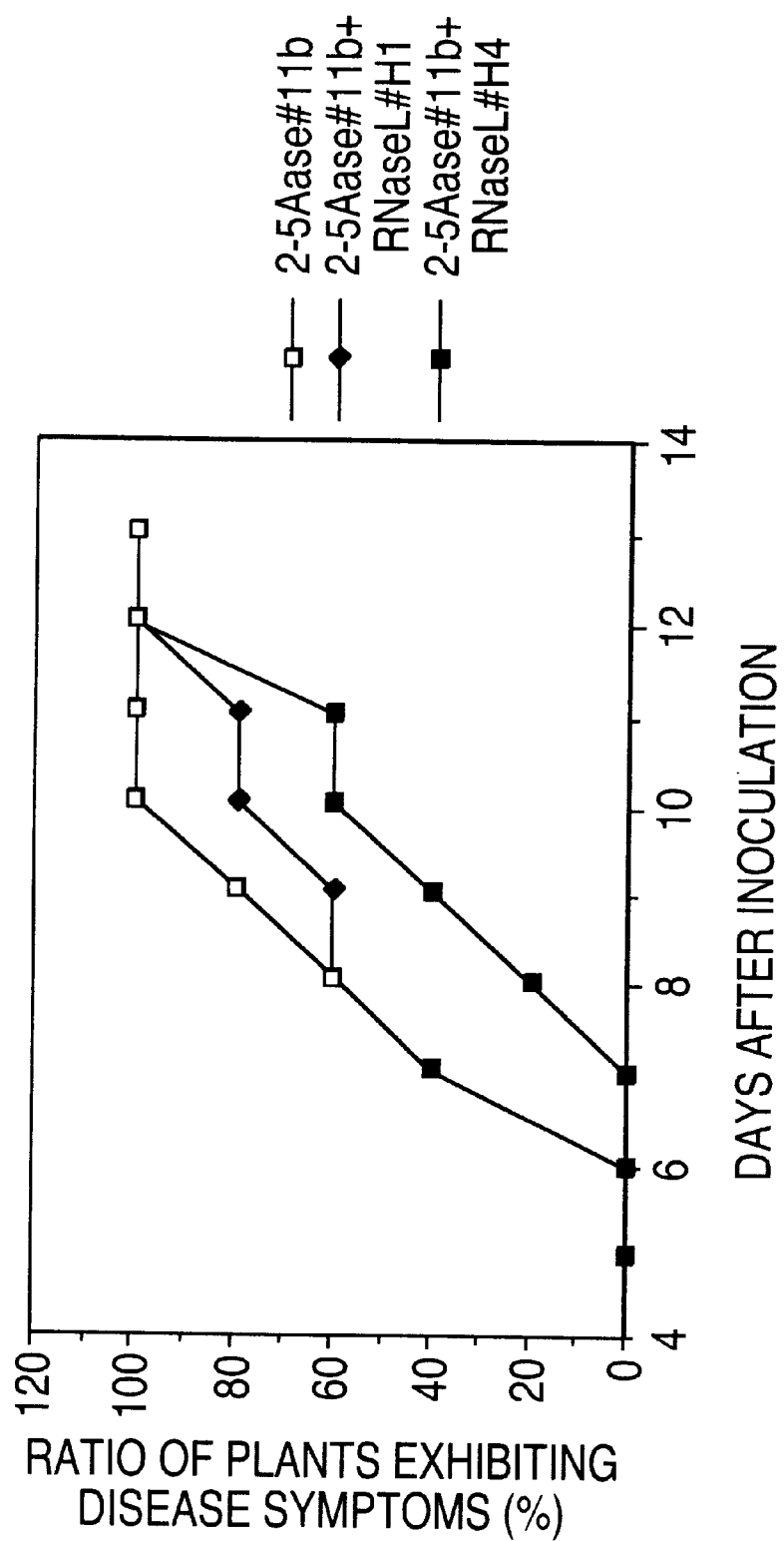
FIG. 5 is a graph showing ratios (%) of the 2-5Aase-introduced tobacco (2-5Aase#11b) individuals and [2-5Aase+partial length RNaseL]-introduced tobacco (2-5Aase#11b+RNaseL#H1, 2-5Aase#11b+RNaseL#H4) individuals in which uninoculated upper leaves exhibited disease symptoms after CMV (Y strain) inoculation.
Figure 6:
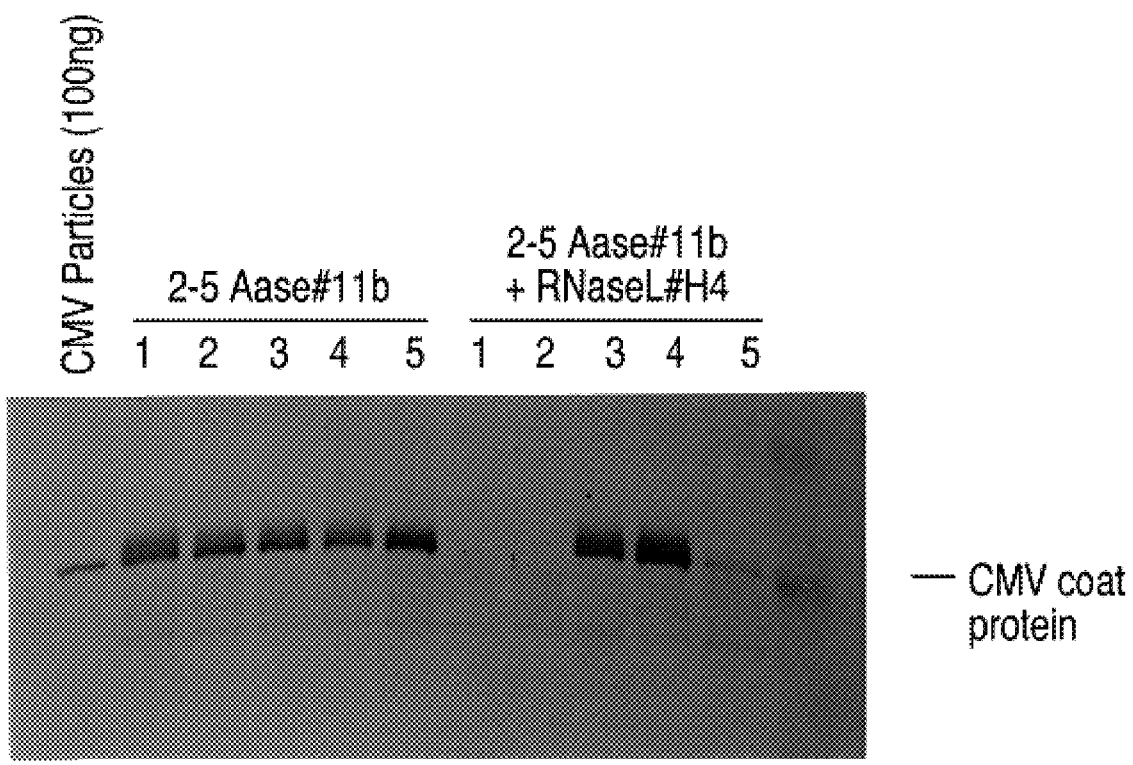
FIG. 6 is a photograph showing the results of electrophoresis to detect CMV coat protein in CMV (Y strain)-inoculated tobacco leaves.

Cucumber Mosaic virus (CMV Y Strain) Infection Experiment(FIGS. 5 and 6)

R1 seeds (2-5Aase-introduced tobacco and 2-5Aase+ RNaseL(T)-introduced tobacco) were sown on MS agar medium containing 800 µg/ml kanamycin or 800 µg/ml kanamycin+100 µg/ml hygromycin to select 2-5Aase-introduced plants or 2-5Aase+RNaseL-introduced plants, respectively. After potting the young plants, DNA was extracted from a part of their leaves (Nuc. Acids Res., 21, 4153, 1993). Then, the presence of 2-5Aase cDNA or RNaseL cDNA was confirmed by PCR. To plants about 2 weeks after potting, 3 µg/ml of CMV Y strain was inoculated, and the development of disease symptoms after viral inoculation was observed. For each transformant, 5 individuals were used. The ratio of plants exhibiting disease symptoms after inoculation in their uninoculated upper leaves was shown in percent. 2-5Aase+RNaseL(T)-introduced tobacco obtained by crossing the activity-confirmed, partial length RNaseL-introduced tobacco (see Example 3 and FIG. 3) with 2-5Aase-introduced tobacco exhibited significantly stronger virus resistance than that of the transformant tobacco into which only 2-5Aase was introduced (FIG. 5). Eight days after inoculation, uninoculated upper leaves were cut off from 5 individuals of each transformant tobacco (2-5Aase#11b and 2-5Aase#11b+ RNaseL#H4) and the total protein was extracted therefrom with 5 volumes of SDS buffer (2% SDS, 80 mM Tris-HCl, pH 6.8, 2% 2-mercaptoethanol, 10% glycerol). Each of the thus obtained sample was diluted 100-fold with SDS electrophoresis sample buffer, and a 10 µl aliquot was fractionated by SDS polyacrylamide gel electrophoresis. The protein was transferred onto a polyvinylidene difluoride (PVDF) membrane (Millipore) to detect CMV in infected plant leaves by color formation with anti-CMV rabbit serum (about 2000-fold dilution) and protein A-alkaline phosphatase. In uninoculated upper leaves of 2-5Aase#11b-introduced tobacco, a strong CMV accumulation was observed in all of the five individuals sampled. On the other hand, in 2-5Aase#11b+RNaseL#H4-introduced tobacco, CMV accumulation was observed only in two individuals out of the five (FIG. 6).

EXAMPLE 6

Cucumber Mosaic Virus (CMV Y Strain) Infection Experiment

Figure 7B:
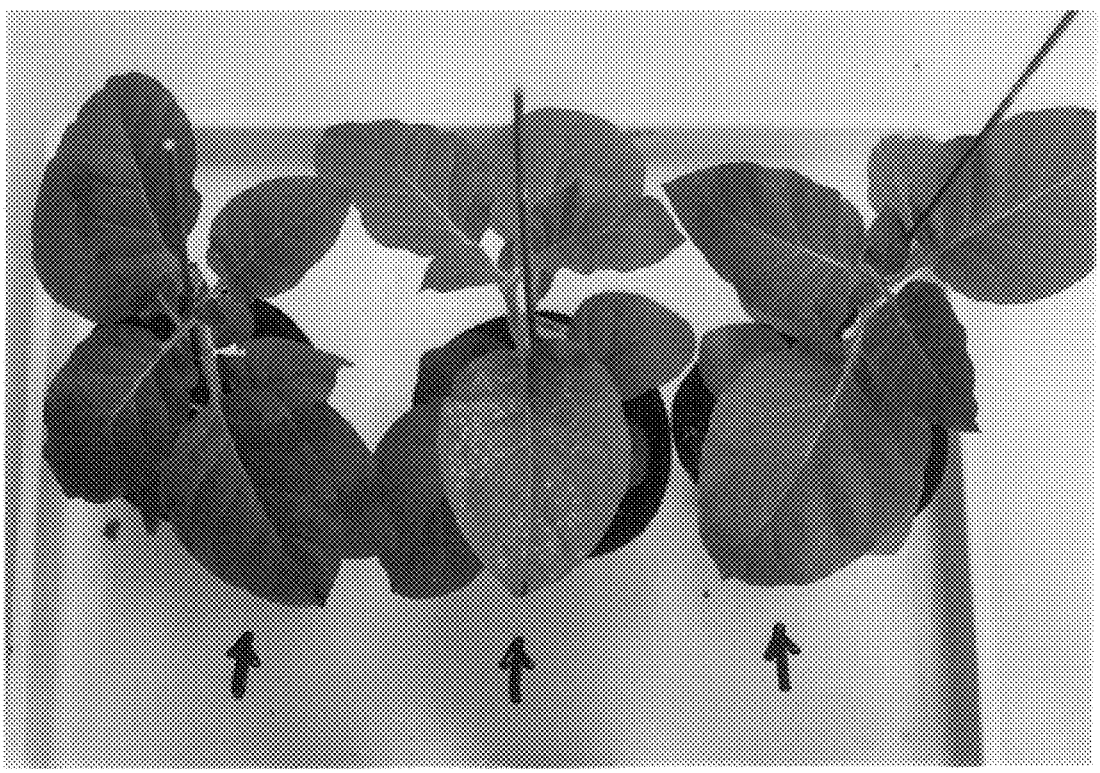

R1 seeds [1 line of 2-5Aase-introduced tobacco (2-5Aase#13b); 3 lines of RNaseL(F)-introduced tobacco (RNaseL(F)#23a, RNaseL(F)#27a, RNaseL(F)#30b)]and F1 seeds [3 lines of 2-5Aase+RNaseL(F)-introduced tobacco (2-5Aase#13b+RNaseL(F)#23a, 2-5Aase#13b+RNaseL(F) #27a, 2-5Aase#13b+RNaseL(F)#30b)] were sown on MS agar medium containing 100 µg/ml hygromycin to select RNaseL(F)-introduced tobacco. After young plants were potted, DNA was extracted from a part of their leaves. Then, the presence of 2-5Aase cDNA or RNaseL(F) cDNA was confirmed by PCR (see Example 5). To plants about 4 weeks after potting, 15 µg/ml of CMV Y strain was inoculated. Then, the time course after viral infection and the development of disease symptoms were observed. For each of the transformant lines, 5 individuals were used for the inoculation experiment. As a result, necrotic spots were observed 3 days after inoculation in inoculated leaves of all the individuals of all the lines in 2-5Aase+RNaseL(F)-introduced tobacco. On the other hand, no necrotic spots were observed in 2-5-Aase-introduced tobacco and RNaseL(F)-introduced tobacco (FIG. 7). Twelve days after inoculation, while disease symptoms were observed in uninoculated upper leaves of all the individuals of all the lines in 2-5Aase-introduced tobacco and RNaseL(F)-introduced tobacco, no disease symptoms were observed in uninoculated upper leaves of all the individuals of all the lines in 2-5Aase+ RNaseL(F)-introduced tobacco (FIG. 8). The total protein was extracted from portions with no necrotic spots in inoculated leaves exhibiting necrotic spots in each transformant tobacco 5 days after infection; and from uninoculated upper leaves of each transformant tobacco 12 days after inoculation by the method described in Example 5, to thereby detect CMV in infected plant leaves. As a result, while a large quantity of CMV was accumulated in inoculated leaves of 2-5Aase-introduced tobacco and RNaseL(F)-introduced tobacco 5 days after infection, CMV was not detected in non-necrotic spot-forming portions of 2-5Aase+ RNaseL(F)-introduced tobacco though a small quantity of CMV was detected in necrotic spots (FIG. 9). Also, in uninoculated upper leaves 12 days after inoculation, while a large quantity of CMV was accumulated in 2-5Aase-introduced tobacco and RNaseL(F)-introduced tobacco, CMV was not detected at all in 2-5Aase+RNaseL(F)-introduced tobacco (FIG. 10). From these results, it is considered as follows: 2-5Aase+RNaseL(F)-introduced tobacco formed necrotic spots in CMV-inoculated leaves and the infected cells died from necrosis to thereby prevent the spreading of virus; thus, no disease symptoms were developed.

EXAMPLE 7

Cucumber Mosaic Virus (CMV Y Strain) Infection Experiment

Using Crude Extract from Infected Leaves as an Inoculum

Using R1 seeds [1 line of 2-5Aase-introduced tobacco (2-5Aase#13b); 2 lines of RNaseL(F)-introduced tobacco (RNaseL(F)#23a, RNaseL(F)#30b)] and F1 seeds [2 lines of 2-5Aase+RNaseL(F)-introduced tobacco (2-5Aase#13b+RNaseL(F)#23a, 2-5Aase#13b+RNaseL(F)#30b)], plants were bred in the same manner as described in Example 6. A crude extract was prepared by infecting a tobacco plant about 2 weeks after potting with CMV Y strain and grinding those tobacco leaves (cv Xanthi nc) exhibiting disease symptoms in 10 times the leaf weight of an extraction buffer (10 mM phosphate buffer, pH 7.0, 20 mM 2-mercaptoethanol). The crude extract was inoculated into tobacco plants about 2 weeks after potting, and the time course after inoculation and the development of disease symptoms were observed. For each of the transformant lines, 2 individuals were used for the inoculation experiment. As a result, similar progress as seen when 15 μg/ml of purified virus was infected in Example 6 was observed. Briefly, necrotic spots were observed 3 days after inoculation in inoculated leaves of all the individuals of all the lines in 2-5Aase+RNaseL(F)-introduced tobacco. On the other hand, no necrotic spots were observed in 2-5Aase-introduced tobacco and RNaseL(F)-introduced tobacco. Inoculated leaves 5 days after inoculation are shown in FIG. 11. Twelve days after infection, while disease symptoms were observed in uninoculated upper leaves of all the individuals of all the lines in 2-5Aase-introduced tobacco and RNaseL(F)-introduced tobacco, no disease symptoms were observed in uninoculated upper leaves of all the individuals of all the lines in 2-5Aase+RNaseL(F)-introduced tobacco. Plants 16 days after inoculation are shown in FIG. 12. These results demonstrate that the resistant reaction of 2-5Aase+RNaseL(F)-introduced tobacco against CMV Y strain does not vary depending on the form of an inoculum (i.e., purified virus or crude extract from infected leaves).

EXAMPLE 8

Potato Virus Y T Strain(PVY T Strain) Infection Experiment

Using R1 seeds [1 line of 2-5Aase-introduced tobacco (2-5Aase#13b); 3 lines of RNaseL(F)-introduced tobacco (RNaseL(F)#23a, RNaseL(F)#27a, RNaseL(F)#30b)] and F1 seeds [3 lines of 2-5Aase+RNaseL(F)-introduced tobacco (2-5Aase#13b+RNaseL(F)#23a, 2-5Aase#13b+RNaseL(F)#27a, 2-5Aase#13b+RNaseL(F)#30b)], plants were bred in the same manner as described in Example 6. A crude extract was prepared by infecting a tobacco plant with PVY T strain and grinding those tobacco leaves (cv Samsun) exhibiting disease symptoms in 10 times the leaf weight of an extraction buffer (10 mM phosphate buffer, pH 7.0, 20 mM 2-mercaptoethanol). The crude extract was inoculated into tobacco plants about 2 weeks after potting, and the time course after inoculation and the development of disease symptoms were observed. For each of the transformant lines, 5 to 7 individuals were used for the inoculation experiment. As a result, as seen when CMV Y strain was inoculated, necrotic spots were observed 3 days after inoculation in inoculated leaves of all the individuals of all the lines in 2-5Aase+RNaseL(F)-introduced tobacco. On the other hand, no necrotic spots were observed in 2-5Aase-introduced tobacco and RNaseL(F)-introduced tobacco. Inoculated leaves 5 days after inoculation are shown in FIG. 13. Five days after inoculation, necrosis began to be formed in uninoculated upper leaves of all the individuals of all the lines in 2-5Aase+RNaseL(F)-introduced tobacco. This necrosis gradually spread and the plants almost completely withered 20 days after inoculation. Plants 14 days after inoculation are shown in FIG. 14. On the other hand, no withered plants were observed in 2-5Aase-introduced tobacco and RNaseL(F)-introduced tobacco. These tobacco plants presented disease symptoms peculiar to PVY T strain.

The total protein was extracted from uninoculated upper leaves of each transformant tobacco 5 days and 10 days after inoculation in the same manner as described in Example 5 to thereby detect the accumulation of PVY T strain. As a result, while the accumulation of PVY T strain was detected in uninoculated upper leaves both 5 days and 10 days after inoculation in 2-5Aase-introduced tobacco and RNaseL(F)-introduced tobacco, no accumulation of PVY T strain was detected in 2-5Aase+RNaseL(F)-introduced tobacco (FIG. 15). From these results, it is considered as follows: necrotic spots were formed in inoculated leaves of 2-5Aase+RNaseL(F)-introduced tobacco and the infected cells died from necrosis; on the other hand, activation of RNaseL has occurred in uninoculated upper leaves also for some unknown reason, which has caused the systemic withering. However, the fact that the accumulation of PVY T strain was not detected in uninoculated upper leaves both 5 days after inoculation when necrosis began to develop and 10 days after inoculation when necrosis was progressing indicates that the immediate cause for the systemic withering was not excessive accumulation of PVY T strain. In the actual scene of agriculture, virus-infected plants are disposed as early as possible in order to avoid the spreading of virus into surrounding plants (secondary infection). The fact that 2-5Aase+RNaseL(F)-introduced tobacco infected with PVY T strain withers without undergoing the process of virus accumulation means that 2-5Aase+RNaseL(F)-introduced plants will not become sources of secondary infection even if they are infected with PVY T strain and that they will wither naturally. Thus, reduction of labor can be expected when such plants are actually cultured.

EXAMPLE 9

Potato Virus Y O Strain (PVY O Strain) Infection Experiment

Using R1 seeds [1 line of 2-5Aase-introduced tobacco (2-SAase#13b); 3 lines of RNaseL(F)-introduced tobacco (RNaseL(F)#23a, RNaseL(F)#27a, RNaseL(F)#30b)] and F1 seeds [3 lines of 2-5Aase+RNaseL(F)-introduced tobacco (2-5Aase#13b+RNaseL(F)#23a, 2-5Aase#13b+RNaseL(F)#27a, 2-5Aase#13b+RNaseL(F)#30b)], plants were bred in the same manner as described in Example 6. A crude extract was prepared by infecting a tobacco plant with PVY O strain and grinding those tobacco leaves (cv Samsun) exhibiting disease symptoms in 10 times the leaf weight of an extraction buffer (10 mM phosphate buffer, pH 7.0, 20 mM 2-mercaptoethanol). The crude extract was inoculated into tobacco plants about 2 weeks after potting, and the time course after inoculation and the development of disease symptoms were observed. For each of the transformant lines, 5 individuals were used for the inoculation experiment. As a result, almost the same results as seen when PVY T strain was inoculated were observed. Briefly, necrotic spots were observed 3 days after inoculation in inoculated leaves of all the individuals of all the lines in 2-5Aase+RNaseL(F)-introduced tobacco. On the other hand, no necrotic spots were observed in 2-5Aase-introduced tobacco and RNaseL(F)-introduced tobacco (FIG. 16). Five days after inoculation, necrosis began to be formed in uninoculated upper leaves of all the individuals of all the lines in 2-5Aase+RNaseL(F)-introduced tobacco. This necrosis gradually spread and the plants almost completely withered 20 days after inoculation. Plants 15 days after inoculation are shown in FIG. 17. On the other hand, no withered plants were observed in 2-5Aase-introduced tobacco and RNaseL(F)-introduced tobacco. These tobacco plants presented disease symptoms peculiar to PVY O strain.

The total protein was extracted from inoculated leaves of each transformant S days after inoculation and from uninoculated upper leaves of each transformant 6 days after inoculation in the same manner as described in Example 5 to thereby detect the accumulation of PVY O strain. As a result, while PVY O strain was accumulated in both the inoculated leaves 5 days after inoculation and the uninoculated upper leaves 6 days after inoculation in 2-5Aase-introduced tobacco and RNaseL(F)-introduced tobacco, no accumulation of PVY O strain was detected in 2-5Aase+RNaseL(F)-introduced tobacco (FIG. 18). From these results, it was found that although 2-5Aase+RNaseL(F)-introduced tobacco also forms necrotic spots in inoculated leaves due to PVY O strain-infection and the infected cells die from necrosis, this tobacco withers without undergoing the process of virus accumulation. Thus, the nature of 2-5Aase+RNaseL(F)-introduced tobacco that it withers when infected with virus is considered not to vary depending on the strain of PVY but to be a reaction against PVY itself. Not only against infection with PVY T strain but also against infection with PVY O strain, reduction of labor can be expected in the culturing of 2-5Aase+RNaseL(F)-introduced tobacco, and yet this tobacco is considered not to become a source of secondary infection.

EXAMPLE 10

Buffer Inoculation

Using F1 seeds [3 lines of 2-5Aase+RNaseL(F)-introduced tobacco (2-5Aase#13b+RNaseL(F)#23a, 2-5Aase#13b+RNaseL(F)#27a, 2-5Aase#13b+RNaseL(F)#30b)], plants were bred in the same manner as described in Example 6. An extraction buffer (10 mM phosphate buffer, pH 7.0 20 mM 2-mercaptoethanol) was inoculated into plants about 2 weeks after potting, and the time course after inoculation and the development of disease symptoms were observed. For each of the transformant lines, 2 individuals were used for the inoculation experiment. As a result, no change was observed even 10 days after inoculation in both inoculated leaves and uninoculated leaves.

This demonstrates that the series of reactions of 2-5Aase+RNaseL(F)-introduced tobacco after viral infection as described above have been caused by the virus, not by some component(s) in the buffer or the act of inoculation itself.

EXAMPLE 11

Cloning of Bovine-Derived 2-5Aase cDNA and Bovine-Derived RNaseL cDNA and Determination of Their Base Sequences Phage DNA was extracted from a bovine spleen-derived phage lambda gt10 cDNA library (Clontech) by the method of Xshida et al. ("Gene Expression Experimental Manual", Chapter 2, published by Kodansha, 1994) and used as a DNA template for PCR. Primers for use In PCR cloning of bovine 2-5Aase and RNaseL cDNA fragments were designed as follows based on the base sequences for human 2-5Aase cDNA (EMBO J., 4. 2249, 1985) and human 2-5RNaseL cDNA (Cell, 72, 753, 1993).

Bovine 2-5Aase:
   5'-TCCAAGGTGGTAAAGGGTGGCTCCTCAG GCAA-3'
   5'-CTCTGAGCTTGGTGGGGCTGCTTCAGGAA-3'

Bovine RNaseL:
   5'-CTGGGGTTCTATGAGAAGCAAGAAGTAGC TGTTGAA-3'
   5'-GACAAGTGTAGTTCTTGAACAGCCTTAAA TATAGA-3'

A PCR was performed by the method of Ishida et al. and the amplified DNA fragments were subcloned into pBluescript SKII⁺ plasmid (Stratagene) ("Gene Expression Experimental Manual", Chapter 2, published by Kodansha, 1994). Base sequences for these PCR-amplified DNA fragments (2-5Aase: 455 bp; RNaseL: 292 bp) were determined. These base sequences were compared with the base sequences for human 2-5Aase and RNaseL, respectively. As a result, homology was recognized [2-5Aase: 80%; RNaseL: 73% (sequences for primers were excluded from the calculation)]. Thus, these PCR-amplified DNA fragments were confirmed to be parts of bovine-derived 2-5Aase cDNA and bovine-derived RNaseL cDNA, respectively.

Using these PCR-amplified DNA fragments as probes, the bovine spleen-derived cDNA phage library was screened to thereby isolate phage clones encoding full length 2-5Aase cDNA and RNaseL cDNA, respectively. DNA was extracted from each of the isolated phage clones and subcloned into pBluescript SKII⁺plasmid as a cDNA insert. Using DNA Sequencer 373A from Applied Biosystems, the DNA sequence was determined by the fluorescent dye terminator method, and the amino acid sequence deduced therefrom was obtained (FIG. 19: bovine 2-5Aase cDNA; FIG. 20: bovine RNaseL cDNA). As a result, it was found that bovine 2-5Aase has homology to human 2-5AaseE18 (EMBO J., 4, 2249, 1985) and mouse 2-5AaseL3 (Virology, 179, 228, 1990).

By expressing the thus obtained bovine 2-5Aase cDNA and bovine RNaseL CDNA in plants, it becomes possible to breed virus resistant plants.

EXAMPLE 12

Transformation of Tobacco Cultivar Samsun (*Nicotiana tabacum* cv Samsun)

Tobacco cultivar Samsun (genotype of N gene: nn) was used for transformation. Transformants [2-5Aase(S) tobacco and RNaseL(S) tobacco] were created by the method described in Example 2 (i.e., by using pBI2-5Aase- or pBIBRNaseL(F)-introduced Agrobacterium LBA4404).

The resultant transformants were potted. Subsequently, R1 seeds were obtained by self-pollination and F1 seeds [2-5Aase(S)+RNaseL(S) tobacco] by crossing.

EXAMPLE 13

Detection of 2-5Aase Activity and RNaseL Activity in 2-5Aase-introduced Transformant Tobacco (Samsun) and RNaseL(F)-introduced Transformant Tobacco (Samsun)

Detection of 2-5Aase activity was performed in the same manner as described in Example 3 and detection of RNaseL activity in the same manner as described in Example 4. The results are shown in FIGS. 21 and 22. Both the 2-5Aase activity in 2-5Aase(S) tobacco and the RNaseL activity in RNaseL(S) tobacco were significantly higher than those in non-transformants.

EXAMPLE 14

Cucumber Mosaic Virus (CMV Y Strain) Infection Experiment on Samsun Transformants Using Crude Extract from Virus-Infected Leaves as an Inoculum Using R1 seeds [2-5Aase-introduced tobacco (2-5Aase (S)#13-10); RNaseL(F)-introduced tobacco (RNaseL(S) #57-6b)] and F1 seeds [2-5Aase+RNaseL(F)-introduced tobacco (2-5Aase(S)#13-10+RNaseL(S)#57-6b)], plants were bred in the same manner as described in Example 6. A crude extract from CMV Y strain-infected leaves was inoculated into plants about 2 weeks after potting as described in Example 7. The time course after inoculation and the development of disease symptoms were observed. For each of the transformant lines, 3 individuals were used for the inoculation experiment. As a result, similar progress as seen when CMV Y strain was inoculated into Xanthi (genotype of N gene: NN) transformants in Examples 6 and 7 was observed. Briefly, necrotic spots were observed 3 days after inoculation in inoculated leaves of all the individuals of all the lines in 2-5Aase+RNaseL(F)-introduced tobacco. On the other hand, no necrotic spots were observed in 2-5Aase-introduced tobacco and RNaseL(F)-introduced tobacco (FIG. 23). Ten days after inoculation, while disease symptoms were observed in uninoculated upper leaves of all the individuals of all the lines in 2-5Aase-introduced tobacco and RNaseL(F)-introduced tobacco, no disease symptoms were observed in uninoculated upper leaves of all the individuals of all the lines in 2-5Aase+RNaseL(F)-introduced tobacco (FIG. 24). These results indicate that the resistant reaction of 2-5Aase+RNaseL(F)-introduced tobacco against CMV Y strain does not depend on the genotype of N gene in the host tobacco.

INDUSTRIAL APPLICABILITY

The 2-5Aase/RNaseL system expresses ribonuclease activity in cytoplasm upon recognition of double-stranded RNA produced when cells are infected with virus, to thereby inhibit viral proliferation. Since RNA viruses generally form double-stranded RNA at the stage of replication, this system is effective against all of the RNA viruses.

Accordingly, the technology of the invention for creating virus resistant plants comprising introducing 2-5Aase and RNaseL into plants by recombinant DNA technology is widely applicable to the breeding of virus resistant plant varieties.

What is claimed is:

1. A method of preventing spread of RNA virus from an RNA virus-infected plant into noninfected plants, comprising
    (A) crossing (i) a first plant that comprises a DNA sequence encoding an animal cell-derived (2'-5') oligoadenylate synthetase with (ii) a second plant that comprises a DNA sequence encoding an animal cell-derived ribonuclease L and
    (B) obtaining via step (A) a transgenic plant that comprises a DNA sequence encoding an animal cell-derived (2'-5') oligoadenylate synthetase and a DNA sequence encoding an animal cell-derived ribonuclease L, such that said transgenic plant undergoes necrosis upon infection with said RNA virus, whereby said transgenic plant has the property of preventing spread of said RNA virus to noninfected plants.

2. The method of claim 1, wherein the DNA sequence encoding an animal cell-derived (2'-5') oligoadenylate synthetase is derived from any one of human, mouse, rat or bovine.

3. The method of claim 2, wherein the DNA sequence encoding an animal cell-derived (2'-5') oligoadenylate synthetase is a cDNA derived from any one of human, mouse, rat or bovine.

4. The method of claim 1, wherein the DNA sequence encoding an animal cell-derived ribonuclease L is derived from human or bovine.

5. The method of claim 4, wherein the DNA sequence encoding an animal cell-derived ribonuclease L is a cDNA derived from human or bovine.

6. The method of claim 1, wherein the DNA sequence encoding an animal cell-derived (2'-5') oligoadenylate synthetase is derived from any one of human, mouse, rat or bovine, and the DNA sequence encoding an animal cell-derived ribonuclease L is derived from human or bovine.

7. The method of claim 6, wherein the DNA sequence encoding an animal cell-derived (2'-5') oligoadenylate synthetase is a cDNA derived from any one of human, mouse, rat or bovine, and the DNA sequence encoding an animal cell-derived ribonuclease L is derived from human or bovine.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 1322 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
      (A) ORGANISM: Human (xi) SEQUENCE DESCRIPTION: SEQ ID NO: 1:

```
GAGGCAGTTC TGTTGCCACT CTCTCTCCTG TCAATGATGG ATCTCAGAAA TACCCCAGCC      60

AAATCTCTGG ACAAGTTCAT TGAAGACTAT CTCTTGCCAG ACACGTGTTT CCGCATGCAA     120

ATCGACCATG CCATTGACAT CATCTGTGGG TTCCTGAAGG AAAGGTGCTT CCGAGGTAGC     180

TCCTACCCTG TGTGTGTGTC CAAGGTGGTA AAGGGTGGCT CCTCAGGCAA GGGCACCACC     240

CTCAGAGGCC GATCTGACGC TGACCTGGTT GTCTTCCTCA GTCCTCTCAC CACTTTTCAG     300

GATCAGTTAA ATCGCCGGGG AGAGTTCATC CAGGAAATTA GGAGACAGCT GGAAGCCTGT     360

CAAAGAGAGA GAGCACTTTC CGTGAAGTTT GAGGTCCAGG CTCCACGCTG GGGCAACCCC     420

CGTGCGCTCA GCTTCGTACT GAGTTCGCTC CAGCTCGGGG AGGGGTGGA GTTCGATGTG      480

CTGCCTGCCT TTGATGCCCT GGGTCAGTTG ACTGGCAGCT ATAAACCTAA CCCCCAAATC     540

TATGTCAAGC TCATCGAGGA GTGCACCGAC CTGCAGAAAG AGGGCGAGTT CTCCACCTGC     600

TTCACAGAAC TACAGAGAGA CTTCCTGAAG CAGCGCCCCA CCAAGCTCAA GAGCCTCATC     660
```

```
CGCCTAGTCA AGCACTGGTA CCAAAATTGT AAGAAGAAGC TTGGGAAGCT GCCACCTCAG        720

TATGCCCTGG AGCTCCTGAC GGTCTATGCT TGGGAGCGAG GGAGCATGAA ACACATTTC         780

AACACAGCCC AAGGATTTCG GACGGTCTTG GAATTAGTCA TAAACTACCA GCAACTCTGC        840

ATCTACTGGA CAAAGTATTA TGACTTTAAA AACCCCATTA TTGAAAAGTA CCTGAGAAGG        900

CAGCTCACGA AACCCAGGCC TGTGATCCTG GACCCGGCGG ACCCTACAGG AAACTTGGGT        960

GGTGGAGACC CAAAGGGTTG GAGGCAGCTG GCACAAGAGG CTGAGGCCTG GCTGAATTAC       1020

CCATGCTTTA AGAATTGGGA TGGGTCCCCA GTGAGCTCCT GGATTCTGCT GGTGAGACCT       1080

CCTGCTTCCT CCCTGCCATT CATCCCTGCC CCTCTCCATG AAGCTTGAGA CATATAGCTG       1140

GAGACCATTC TTTCCAAAGA ACTTACCTCT TGCCAAAGGC CATTTATATT CATATAGTGA       1200

CAGGCTGTGC TCCATATTTT ACAGTCATTT TGGTCACAAT CGAGGGTTTC TGGAATTTTC       1260

ACATCCCTTG TCCAGAATTC ATTCCCCTAA GAGTAATAAT AAATAATCTC TAACACCAAA       1320

AA                                                                     1322

(2) INFORMATION FOR SEQ ID NO: 2:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO: 2:

TTATTGAAAA GTACCTGAGA AGGCAGCTCA CGAAACCCAG GCCTGTGATC                    50

(2) INFORMATION FOR SEQ ID NO: 3:

(i) SEQUENCE CHARACTERISTICS:
        (A) LENGTH: 2378 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
         (A) ORGANISM: human (xi) SEQUENCE DESCRIPTION: SEQ ID NO: 3:

CTTTGATTAA GTGCTAGGAG ATAAATTTGC ATTTTCTCAA GGAAAAGGCT AAAAGTGGTA         60

GCAGGTGGCA TTTACCGTCA TGGAGAGCAG GGATCATAAC AACCCCCAGG AGGGACCCAC        120

GTCCTCCAGC GGTAGAAGGG CTGCAGTGGA AGACAATCAC TTGCTGATTA AAGCTGTTCA        180

AAACGAAGAT GTTGACCTGG TCCAGCAATT GCTGGAAGGT GGAGCCAATG TTAATTTCCA        240

GGAAGAGGAA GGGGGCTGGA CACCTCTGCA TAACGCAGTA CAAATGAGCA GGGAGGACAT        300

TGTGGAACTT CTGCTTCGTC ATGGTGCTGA CCCTGTTCTG AGGAAGAAGA ATGGGGCCAC        360

GCCTTTTATC CTCGCAGCGA TTGCGGGGAG CGTGAAGCTG CTGAAACTTT CCTTTCTAA         420

AGGAGCAGAT GTCAATGAGT GTGATTTTTA TGGCTTCACA GCCTTCATGG AAGCCGCTGT        480

GTATGGTAAG GTCAAAGCCC TAAAATTCCT TTATAAGAGA GGAGCAAATG TGAATTTGAG        540

GCGAAAGACA AAGGAGGATC AAGAGCGGCT GAGGAAAGGA GGGGCCACAG CTCTCATGGA        600

CGCTGCTGAA AAAGGACACG TAGAGGTCTT GAAGATTCTC CTTGATGAGA TGGGGGCAGA        660

TGTAAACGCC TGTGACAATA TGGGCAGAAA TGCCTTGATC CATGCTCTCC TGAGCTCTGA        720
```

```
CGATAGTGAT GTGGAGGCTA TTACGCATCT GCTGCTGGAC CATGGGCTG ATGTCAATGT      780

GAGGGGAGAA AGAGGGAAGA CTCCCCTGAT CCTGGCAGTG GAGAAGAAGC ACTTGGGTTT      840

GGTGCAGAGG CTTCTGGAGC AAGAGCACAT AGAGATTAAT GACACAGACA GTGATGGCAA      900

AACAGCACTG CTGCTTGCTG TTGAACTCAA ACTGAAGAAA ATCGCCGAGT TGCTGTGCAA      960

ACGTGGAGCC AGTACAGATT GTGGGGATCT TGTTATGACA GCGAGGCGGA ATTATGACCA     1020

TTCCCTTGTG AAGGTTCTTC TCTCTCATGG AGCCAAAGAA GATTTTCACC CTCCTGCTGA     1080

AGACTGGAAG CCTCAGAGCT CACACTGGGG GGCAGCCCTG AAGGATCTCC ACAGAATATA     1140

CCGCCCTATG ATTGGCAAAC TCAAGTTCTT TATTGATGAA AAATACAAAA TTGCTGATAC     1200

TTCAGAAGGA GGCATCTACC TGGGGTTCTA TGAGAAGCAA GAAGTAGCTG TGAAGACGTT     1260

CTGTGAGGGC AGCCCACGTG CACAGCGGGA AGTCTCTTGT CTGCAAAGCA GCCGAGAGAA     1320

CAGTCACTTG GTGACATTCT ATGGGAGTGA GAGCCACAGG GGCCACTTGT TTGTGTGTGT     1380

CACCCTCTGT GAGCAGACTC TGGAAGCGTG TTTGGATGTG CACAGAGGGG AAGATGTGGA     1440

AAATGAGGAA GATGAATTTG CCCGAAATGT CCTGTCATCT ATATTTAAGG CTGTTCAAGA     1500

ACTACACTTG TCCTGTGGAT ACACCCACCA GGATCTGCAA CCACAAAACA TCTTAATAGA     1560

TTCTAAGAAA GCTGCTCACC TGGCAGATTT TGATAAGAGC ATCAAGTGGG CTGGAGATCC     1620

ACAGGAAGTC AAGAGAGATC TAGAGGACCT TGGACGGCTG GTCCTCTATG TGGTAAAGAA     1680

GGGAAGCATC TCATTTGAGG ATCTGAAAGC TCAAAGTAAT GAAGAGGTGG TTCAACTTTC     1740

TCCAGATGAG GAAACTAAGG ACCTCATTCA TCGTCTCTTC CATCCTGGGG AACATGTGAG     1800

GGACTGTCTG AGTGACCTGC TGGGTCATCC CTTCTTTTGG ACTTGGGAGA GCCGCTATAG     1860

GACGCTTCGG AATGTGGGAA ATGAATCCGA CATCAAAACA CGAAAATCTG AAAGTGAGAT     1920

CCTCAGACTA CTGCAACCTG GGCCTTCTGA ACATTCCAAA AGTTTTGACA AGTGGACGAC     1980

TAAGATTAAT GAATGTGTTA TGAAAAAAAT GAATAAGTTT TATGAAAAAA GAGGCAATTT     2040

CTACCAGAAC ACTGTGGGTG ATCTGCTAAA GTTCATCCGG AATTTGGGAG AACACATTGA     2100

TGAAGAAAAG CATAAAAAGA TGAAATTAAA AATTGGAGAC CCTTCCCTGT ATTTTCAGAA     2160

GACATTTCCA GATCTGGTGA TCTATGTCTA CACAAAACTA CAGAACACAG AATATAGAAA     2220

GCATTTCCCC CAAACCCACA GTCCAAACAA ACCTCAGTGT GATGGAGCTG GTGGGCCAG     2280

TGGGTTGGCC AGCCCTGGGT GCTGATGGAC TGATTTGCTG GAGTTCAGGG AACTACTTAT     2340

TAGCTGTAGA GTCCTTGGCA AATCACAACA TTCTGGGC                             2378
```

(2) INFORMATION FOR SEQ ID NO: 4:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 4:

```
AATGGGGCCA CGCTTTTTAT CCTCGCAGCG ATTGCGGGGA GCGTGAAGCT G              51
```

(2) INFORMATION FOR SEQ ID NO: 5:

(i) SEQUENCE CHARACTERISTICS:
        (A) LENGTH: 32 base pairs
        (B) TYPE: nucleic acid (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 5:

TCCAAGGTGG TAAAGGGTGG CTCCTCAGGC AA                32

(2) INFORMATION FOR SEQ ID NO: 6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 6:

CTCTTGAGCT TGGTGGGGCG CTGCTTCAGG AA                32

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 7:

CTGGGGTTCT ATGAGAAGCA AGAAGTAGCT GTGAA             35

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 8:

GACAAGTGTA GTTCTTGAAC AGCCTTAAAT ATAGA             35

(2) INFORMATION FOR SEQ ID NO: 9:

(i) SEQUENCE CHARACTERISTICS:
        (A) LENGTH: 1170 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: bovine (ix) FEATURE:
        (A) NAME/KEY: CDS
        (B) LOCATION:1..1167

(xi) SEQUENCE DESCRIPTION: SEQ ID NO: 9:

ATG GAA CTC AGA TAT ACC CCG GCC GGG TCT CTA GAC AAG TTC ATC CAA        48

```
Met Glu Leu Arg Tyr Thr Pro Ala Gly Ser Leu Asp Lys Phe Ile Gln
 1               5                  10                  15

GTC CAC CTC CTG CCA AAC GAA GAA TTC AGC ACG CAG GTC CAA GAA GCC        96
Val His Leu Leu Pro Asn Glu Glu Phe Ser Thr Gln Val Gln Glu Ala
             20                  25                  30

ATC GAC ATC ATC TGC ACT TTC CTG AAG GAA AAG TGT TTC CGA TGT GCC       144
Ile Asp Ile Ile Cys Thr Phe Leu Lys Glu Lys Cys Phe Arg Cys Ala
             35                  40                  45

CCT CAC AGA GTT CGG GTG TCC AAA GTT GTG AAG GGC GGC TCC TCA GGC       192
Pro His Arg Val Arg Val Ser Lys Val Val Lys Gly Gly Ser Ser Gly
     50                  55                  60

AAA GGC ACG ACC CTC AGG GGA CGA TCA GAT GCT GAC CTC GTC GTC TTC       240
Lys Gly Thr Thr Leu Arg Gly Arg Ser Asp Ala Asp Leu Val Val Phe
 65                  70                  75                  80

CTC ACC AAT CTC ACA AGT TTT CAG GAA CAG CTT GAG CGC CGA GGA GAA       288
Leu Thr Asn Leu Thr Ser Phe Gln Glu Gln Leu Glu Arg Arg Gly Glu
                 85                  90                  95

TTC ATT GAA GAA ATC AGG AGA CAG CTG GAA GCC TGT CAA AGA GAG GAA       336
Phe Ile Glu Glu Ile Arg Arg Gln Leu Glu Ala Cys Gln Arg Glu Glu
                 100                 105                 110

ACA TTT GAA GTG AAG TTT GAG GTC CAG AAA CGG CAA TGG GAG AAT CCC       384
Thr Phe Glu Val Lys Phe Glu Val Gln Lys Arg Gln Trp Glu Asn Pro
         115                 120                 125

CGC GCT CTC AGC TTT GTG CTG AGG TCC CCC AAG CTC AAC CAG GCG GTG       432
Arg Ala Leu Ser Phe Val Leu Arg Ser Pro Lys Leu Asn Gln Ala Val
     130                 135                 140

GAG TTC TAT GTC CTG CCC GCC TTT GAT GCC CTA GGT CAG TTG ACC AAA       480
Glu Phe Tyr Val Leu Pro Ala Phe Asp Ala Leu Gly Gln Leu Thr Lys
145                 150                 155                 160

GGT TAC AGA CCT GAC TCT AGA GTC TAT GTC CGG CTC ATC CAA GAG TGC       528
Gly Tyr Arg Pro Asp Ser Arg Val Tyr Val Arg Leu Ile Gln Glu Cys
                 165                 170                 175

GAG AAC CTG AGG AGA GAG GGC GAG TTC TCC CCC TGC TTC ACG GAG CTG       576
Glu Asn Leu Arg Arg Glu Gly Glu Phe Ser Pro Cys Phe Thr Glu Leu
                 180                 185                 190

CAG CGA GAC TTC CTG AAG AAT CGT CCA ACC AAG CTG AAG AAC CTC ATC       624
Gln Arg Asp Phe Leu Lys Asn Arg Pro Thr Lys Leu Lys Asn Leu Ile
         195                 200                 205

CGC CTG GTG AAG CAC TGG TAC CAA CTG TGT AAG GAG CAG CTT GGA AAG       672
Arg Leu Val Lys His Trp Tyr Gln Leu Cys Lys Glu Gln Leu Gly Lys
     210                 215                 220

CCA TTG CCC CCA CAA TAT GCT CTG GAG CTT CTG ACG GTC TAT GCC TGG       720
Pro Leu Pro Pro Gln Tyr Ala Leu Glu Leu Leu Thr Val Tyr Ala Trp
225                 230                 235                 240

GAA CAA GGA TGC AAT AAA ACA GGA TTC ATC ACA GCT CAG GGA TTT CAG       768
Glu Gln Gly Cys Asn Lys Thr Gly Phe Ile Thr Ala Gln Gly Phe Gln
                 245                 250                 255

ACT GTC TTG AAA TTA GTC CTA AAG TAT CAG AAG CTT TGC ATC TAC TGG       816
Thr Val Leu Lys Leu Val Leu Lys Tyr Gln Lys Leu Cys Ile Tyr Trp
                 260                 265                 270

GAA AAG AAC TAT AAC TCT GAA AAC CCT ATT ATT GAA GAA TAT CTG ACG       864
Glu Lys Asn Tyr Asn Ser Glu Asn Pro Ile Ile Glu Glu Tyr Leu Thr
         275                 280                 285

AAG CAA CTT GCA AAA CCC AGG CCT GTG ATT CTG GAC CCG GCG GAC CCT       912
Lys Gln Leu Ala Lys Pro Arg Pro Val Ile Leu Asp Pro Ala Asp Pro
     290                 295                 300

ACA GGA AAT GTT GCT GGT AAA GAC GCA TAT AGC TGG GAA CGG CTT GCA       960
Thr Gly Asn Val Ala Gly Lys Asp Ala Tyr Ser Trp Glu Arg Leu Ala
305                 310                 315                 320
```

```
CGA ACG GCT TTG GTC TGG CTG GAT TAC CCG TGC TTT AAG AAA TGG GAT      1008
Arg Thr Ala Leu Val Trp Leu Asp Tyr Pro Cys Phe Lys Lys Trp Asp
            325                 330                 335

GGG TCT CCC GTG GGC TCC TGG GAT GTG TCG CCC CAA GAA CAC AGT GAC      1056
Gly Ser Pro Val Gly Ser Trp Asp Val Ser Pro Gln Glu His Ser Asp
                340                 345                 350

CTG ATG TTC CAG GCC TAT GAT TTT AGA CAG CAC TAT AGA CCC TCT CCA      1104
Leu Met Phe Gln Ala Tyr Asp Phe Arg Gln His Tyr Arg Pro Ser Pro
            355                 360                 365

GGA ATC CAG TTC CAC GGA GGA GCC TCT CCC CAG GTG GAA GAG AAC TGG      1152
Gly Ile Gln Phe His Gly Gly Ala Ser Pro Gln Val Glu Glu Asn Trp
    370                 375                 380

ACA TGT ACC ATC CTC TGA                                              1170
Thr Cys Thr Ile Leu
385
```

(2) INFORMATION FOR SEQ ID NO: 10:

(i) SEQUENCE CHARACTERISTICS:
        (A) LENGTH: 2157 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: bovine (ix) FEATURE:
        (A) NAME/KEY: CDS
        (B) LOCATION:1..2154

(xi) SEQUENCE DESCRIPTION: SEQ ID NO: 10:

```
ATG GAG ACT GAG AGC CAT AAC AAC CCT CAG GAA AGA CCC ACA CCC TCT       48
Met Glu Thr Glu Ser His Asn Asn Pro Gln Glu Arg Pro Thr Pro Ser
 1               5                  10                  15

AGT AAT GGG AAG GCT TCA ATG GGA GAC AAT CAT TCG TTG ATT AAA GCT       96
Ser Asn Gly Lys Ala Ser Met Gly Asp Asn His Ser Leu Ile Lys Ala
                20                  25                  30

GTT AGA GAT GAA GAC ATT GAG TCG GTC CAG CAA TTG CTA GAA AGA GGG      144
Val Arg Asp Glu Asp Ile Glu Ser Val Gln Gln Leu Leu Glu Arg Gly
            35                  40                  45

GCT GAT GTC AAT TTC CAG GAA GAA TGG GGC TGG TCA CCT TTG CAT AAT      192
Ala Asp Val Asn Phe Gln Glu Glu Trp Gly Trp Ser Pro Leu His Asn
 50                  55                  60

GCA GTA CAA GTT GAC AGA GAG GAC ATT GTG GAA CTT CTG CTT AGT CAT      240
Ala Val Gln Val Asp Arg Glu Asp Ile Val Glu Leu Leu Leu Ser His
 65                  70                  75                  80

GGT GCT GAG CCT TGT CTG CGG AAG AAG AAT GGG GCC ACT CCC TTC ATC      288
Gly Ala Glu Pro Cys Leu Arg Lys Lys Asn Gly Ala Thr Pro Phe Ile
                85                  90                  95

ATT GCT GGG ATT GTG GGA AAC GTG AAG TTG CTC AAA CTA TTA CTT CCT      336
Ile Ala Gly Ile Val Gly Asn Val Lys Leu Leu Lys Leu Leu Leu Pro
                100                 105                 110

AAA GTA ACA GAT GTC AAT GAG TGT GAT GTT AAT GGC TTC ACA GCT TTC      384
Lys Val Thr Asp Val Asn Glu Cys Asp Val Asn Gly Phe Thr Ala Phe
            115                 120                 125

ATG GAA GCT GCT GTG TAT GGC AAA GTC GAA GCC TTA AGA TTC CTG TAT      432
Met Glu Ala Ala Val Tyr Gly Lys Val Glu Ala Leu Arg Phe Leu Tyr
        130                 135                 140

AAC AAC GGA GCA GAG GTG AAT TTG CAC AGA AAG ACA ATA GAG GAT CAA      480
Asn Asn Gly Ala Glu Val Asn Leu His Arg Lys Thr Ile Glu Asp Gln
145                 150                 155                 160
```

```
GAG AGG GTT AAG AAA GGA GGG GCC ACT GCT CTC ATG GAT GCT GCT AGA          528
Glu Arg Val Lys Lys Gly Gly Ala Thr Ala Leu Met Asp Ala Ala Arg
            165                 170                 175

AGA GGG CAT GTA GAT GTC GTA GAG ATC CTC CTT CAT GAG ATG GGG GCA          576
Arg Gly His Val Asp Val Val Glu Ile Leu Leu His Glu Met Gly Ala
                180                 185                 190

GAT GTC AAT GCT CGG GAC AAT AGG GGC AGA AAT GCT TTA ATC TAT GCT          624
Asp Val Asn Ala Arg Asp Asn Arg Gly Arg Asn Ala Leu Ile Tyr Ala
            195                 200                 205

CTT CTG AAC TCT GAT GAT GAG AAG GTG AAA GTG AAA GCN ACT ACT CGC          672
Leu Leu Asn Ser Asp Asp Glu Lys Val Lys Val Lys Ala Thr Thr Arg
    210                 215                 220

CTT CTG CTG GAC TAT AAG GTT GAT GTC AAT GTG AGG GGG GAA GGA AGG          720
Leu Leu Leu Asp Tyr Lys Val Asp Val Asn Val Arg Gly Glu Gly Arg
225                 230                 235                 240

AAG ACG CCG CTG ATC TTG GCA GTG GAA AAG AAG AAC CTG GAT CTG GTG          768
Lys Thr Pro Leu Ile Leu Ala Val Glu Lys Lys Asn Leu Asp Leu Val
                245                 250                 255

CAG ATG CTT CTG GAA CAA ACA GCT ATA GAG ATT AAT GAC ACA GAC AGT          816
Gln Met Leu Leu Glu Gln Thr Ala Ile Glu Ile Asn Asp Thr Asp Ser
            260                 265                 270

GAG GGT AAA ACA GCA CTG CTG CTT GCT GTC GAG CTC AAG CTG AAG GAA          864
Glu Gly Lys Thr Ala Leu Leu Leu Ala Val Glu Leu Lys Leu Lys Glu
        275                 280                 285

ATT GCC CAG TTG CTG TGT CGC AAA GGA GCC AGC ACA AAA TGC GGG GAC          912
Ile Ala Gln Leu Leu Cys Arg Lys Gly Ala Ser Thr Lys Cys Gly Asp
    290                 295                 300

CTC GTC GCA ATA GCG AAG CGC AAT TAT GAC TCT GAC CTT GCA AAG TTC          960
Leu Val Ala Ile Ala Lys Arg Asn Tyr Asp Ser Asp Leu Ala Lys Phe
305                 310                 315                 320

CTT CGC CAG CAT GGA GCT GTA GAA GAC GTT TGC CCT CCT GCT AAA GCC         1008
Leu Arg Gln His Gly Ala Val Glu Asp Val Cys Pro Pro Ala Lys Ala
                325                 330                 335

TGG AAG CCT CAG AGC TCA CGT TGG GGG GAG GCC CTG AAA CAT CTT CAC         1056
Trp Lys Pro Gln Ser Ser Arg Trp Gly Glu Ala Leu Lys His Leu His
            340                 345                 350

AGG ATA TAC CGC CCT ATG ATA GGC AAA CTC AAG ATC TTT ATT GAT GAA         1104
Arg Ile Tyr Arg Pro Met Ile Gly Lys Leu Lys Ile Phe Ile Asp Glu
        355                 360                 365

GAA TAT AAA ATC GCT GAC ACT TCC CAA GGG GGC ATC TAC CTG GGG TTA         1152
Glu Tyr Lys Ile Ala Asp Thr Ser Gln Gly Gly Ile Tyr Leu Gly Leu
370                 375                 380

TAT GAG GAA CAA GAG GTA GCT GTG AAG CGG TTC CCT AAA GGC AGC ACA         1200
Tyr Glu Glu Gln Glu Val Ala Val Lys Arg Phe Pro Lys Gly Ser Thr
385                 390                 395                 400

CGG GGA CAA AAT GAA GTC TCT TGT TTG CAG AGC AAC CGA GCC AAT GGT         1248
Arg Gly Gln Asn Glu Val Ser Cys Leu Gln Ser Asn Arg Ala Asn Gly
                405                 410                 415

CAC GTG GTG ACG TTC TAT GGC AGT GAG AGC GAC AGG ACC TGT CTG TAT         1296
His Val Val Thr Phe Tyr Gly Ser Glu Ser Asp Arg Thr Cys Leu Tyr
            420                 425                 430

GTG TGC TTG GCC CTG TGT GAG CAC ACG CTG GAG AAG CAC TTG GAC GAC         1344
Val Cys Leu Ala Leu Cys Glu His Thr Leu Glu Lys His Leu Asp Asp
        435                 440                 445

CGC AAA GGA GAG GCT GTG CAA AAC AAG GAA GAT GAA TTT GCC CGC AAC         1392
Arg Lys Gly Glu Ala Val Gln Asn Lys Glu Asp Glu Phe Ala Arg Asn
    450                 455                 460

ATC CTC TCA TCT CTG TTT AAG GCT GTT GAG GAA CTA CAC CGG TCT GGA         1440
Ile Leu Ser Ser Leu Phe Lys Ala Val Glu Glu Leu His Arg Ser Gly
```

```
465                470                475                480
TAC ACT CAT CAG GAT CTG CAA CCG CAG AAC ATC TTA ATA GAT TCC AAG      1488
Tyr Thr His Gln Asp Leu Gln Pro Gln Asn Ile Leu Ile Asp Ser Lys
                    485                490                495

AAT GGT GCT TGC CTG GCA GAT TTT GAT AAA AGC GTC AAG GGG ACT GGA      1536
Asn Gly Ala Cys Leu Ala Asp Phe Asp Lys Ser Val Lys Gly Thr Gly
                500                505                510

GAT CCA CAG GAA ATC AAG AGA GAT CTA GAG GCC CTG GGA CTG CTG GTC      1584
Asp Pro Gln Glu Ile Lys Arg Asp Leu Glu Ala Leu Gly Leu Leu Val
            515                520                525

CTA TAT GTG GTA AAA AAG GGA AAT GAT TCT TTT GAG ATG CTG AAG AAT      1632
Leu Tyr Val Val Lys Lys Gly Asn Asp Ser Phe Glu Met Leu Lys Asn
        530                535                540

CTA AGA ACT GAA GAG TTG ATT GAG CGT TCT CCA GAT AAG GAA ACT CGG      1680
Leu Arg Thr Glu Glu Leu Ile Glu Arg Ser Pro Asp Lys Glu Thr Arg
545                550                555                560

GAC CTC ATT CGG CAT CTG TTA GTC CCT GGG GAC AAT GTG AAG GGC CAT      1728
Asp Leu Ile Arg His Leu Leu Val Pro Gly Asp Asn Val Lys Gly His
                565                570                575

CTG AGT GGC CTG CTG GCT CAT CCC TTC TTT TGG AGT TGG GAG AGC CGC      1776
Leu Ser Gly Leu Leu Ala His Pro Phe Phe Trp Ser Trp Glu Ser Arg
                580                585                590

TAC CGG ACC CTA CGG GAT GTG GGA AAC GAA TCT GAC ATC AAA ACA CGA      1824
Tyr Arg Thr Leu Arg Asp Val Gly Asn Glu Ser Asp Ile Lys Thr Arg
            595                600                605

AAT ACT AAT GGC AAG ATC CTC CAG CTT CTG CAA CCT GAA ACA TCT GAA      1872
Asn Thr Asn Gly Lys Ile Leu Gln Leu Leu Gln Pro Glu Thr Ser Glu
        610                615                620

CTT CCA AGT TTT GCC CAG TGG ACA ATT GAG GTT GAC AAA TCT GTG ATG      1920
Leu Pro Ser Phe Ala Gln Trp Thr Ile Glu Val Asp Lys Ser Val Met
625                630                635                640

AAA AAA ATG AAT ACC TAT CAG AAC ACT GTA GGT GAC CTG CTG AAG TTC      1968
Lys Lys Met Asn Thr Tyr Gln Asn Thr Val Gly Asp Leu Leu Lys Phe
                645                650                655

ATC CGG AAT GTG GGA GAG CAC ATT AAT GAA CAA AAG AAT ATA GAG ATG      2016
Ile Arg Asn Val Gly Glu His Ile Asn Glu Gln Lys Asn Ile Glu Met
                660                665                670

AAG TCA AAA ATT GGA GAA CCT TCC CAG TAT TTT CAG GAG AAA TTT CCA      2064
Lys Ser Lys Ile Gly Glu Pro Ser Gln Tyr Phe Gln Glu Lys Phe Pro
            675                680                685

GAT CTG GTC ATG TAT GTC TAT AAA AGA CTA CAG AAC ACA GAA TAT GCA      2112
Asp Leu Val Met Tyr Val Tyr Lys Arg Leu Gln Asn Thr Glu Tyr Ala
        690                695                700

AAG CAT TTT CCA AAA AAT CTC AAC CTG AAC AAA CCC GAC GTG              2154
Lys His Phe Pro Lys Asn Leu Asn Leu Asn Lys Pro Asp Val
705                710                715

TGA                                                                   2157

(2) INFORMATION FOR SEQ ID NO: 11:

(i) SEQUENCE CHARACTERISTICS:
        (A) LENGTH: 389 amino acids
        (B) TYPE: amino acid
        (D) TOPOLOGY: linear (ii) MOLECULE TYPE: protein (xi) SEQUENCE DESCRIPTION: SEQ ID NO: 11:

Met Glu Leu Arg Tyr Thr Pro Ala Gly Ser Leu Asp Lys Phe Ile Gln
 1               5                  10                  15
```

```
Val His Leu Leu Pro Asn Glu Glu Phe Ser Thr Gln Val Gln Glu Ala
             20                  25                  30

Ile Asp Ile Ile Cys Thr Phe Leu Lys Glu Lys Cys Phe Arg Cys Ala
         35                  40                  45

Pro His Arg Val Arg Val Ser Lys Val Val Lys Gly Gly Ser Ser Gly
     50                  55                  60

Lys Gly Thr Thr Leu Arg Gly Arg Ser Asp Ala Asp Leu Val Val Phe
 65                  70                  75                  80

Leu Thr Asn Leu Thr Ser Phe Gln Glu Gln Leu Glu Arg Arg Gly Glu
                 85                  90                  95

Phe Ile Glu Glu Ile Arg Arg Gln Leu Glu Ala Cys Gln Arg Glu Glu
             100                 105                 110

Thr Phe Glu Val Lys Phe Glu Val Gln Lys Arg Gln Trp Glu Asn Pro
         115                 120                 125

Arg Ala Leu Ser Phe Val Leu Arg Ser Pro Lys Leu Asn Gln Ala Val
     130                 135                 140

Glu Phe Tyr Val Leu Pro Ala Phe Asp Ala Leu Gly Gln Leu Thr Lys
145                 150                 155                 160

Gly Tyr Arg Pro Asp Ser Arg Val Tyr Val Arg Leu Ile Gln Glu Cys
                 165                 170                 175

Glu Asn Leu Arg Arg Glu Gly Glu Phe Ser Pro Cys Phe Thr Glu Leu
             180                 185                 190

Gln Arg Asp Phe Leu Lys Asn Arg Pro Thr Lys Leu Lys Asn Leu Ile
         195                 200                 205

Arg Leu Val Lys His Trp Tyr Gln Leu Cys Lys Glu Gln Leu Gly Lys
     210                 215                 220

Pro Leu Pro Pro Gln Tyr Ala Leu Glu Leu Leu Thr Val Tyr Ala Trp
225                 230                 235                 240

Glu Gln Gly Cys Asn Lys Thr Gly Phe Ile Thr Ala Gln Gly Phe Gln
                 245                 250                 255

Thr Val Leu Lys Leu Val Leu Lys Tyr Gln Lys Leu Cys Ile Tyr Trp
             260                 265                 270

Glu Lys Asn Tyr Asn Ser Glu Asn Pro Ile Ile Glu Glu Tyr Leu Thr
         275                 280                 285

Lys Gln Leu Ala Lys Pro Arg Pro Val Ile Leu Asp Pro Ala Asp Pro
     290                 295                 300

Thr Gly Asn Val Ala Gly Lys Asp Ala Tyr Ser Trp Glu Arg Leu Ala
305                 310                 315                 320

Arg Thr Ala Leu Val Trp Leu Asp Tyr Pro Cys Phe Lys Lys Trp Asp
                 325                 330                 335

Gly Ser Pro Val Gly Ser Trp Asp Val Ser Pro Gln Glu His Ser Asp
             340                 345                 350

Leu Met Phe Gln Ala Tyr Asp Phe Arg Gln His Tyr Arg Pro Ser Pro
         355                 360                 365

Gly Ile Gln Phe His Gly Gly Ala Ser Pro Gln Val Glu Glu Asn Trp
     370                 375                 380

Thr Cys Thr Ile Leu
385

(2) INFORMATION FOR SEQ ID NO: 12:

(i) SEQUENCE CHARACTERISTICS:
        (A) LENGTH: 718 amino acids
        (B) TYPE: amino acid
        (D) TOPOLOGY: linear
```

(ii) MOLECULE TYPE: protein (xi) SEQUENCE DESCRIPTION: SEQ ID NO: 12:

```
Met Glu Thr Glu Ser His Asn Asn Pro Gln Glu Arg Pro Thr Pro Ser
  1               5                  10                  15

Ser Asn Gly Lys Ala Ser Met Gly Asp Asn His Ser Leu Ile Lys Ala
             20                  25                  30

Val Arg Asp Glu Asp Ile Glu Ser Val Gln Gln Leu Leu Glu Arg Gly
         35                  40                  45

Ala Asp Val Asn Phe Gln Glu Glu Trp Gly Trp Ser Pro Leu His Asn
     50                  55                  60

Ala Val Gln Val Asp Arg Glu Asp Ile Val Glu Leu Leu Leu Ser His
 65                  70                  75                  80

Gly Ala Glu Pro Cys Leu Arg Lys Lys Asn Gly Ala Thr Pro Phe Ile
                 85                  90                  95

Ile Ala Gly Ile Val Gly Asn Val Lys Leu Leu Lys Leu Leu Leu Pro
                100                 105                 110

Lys Val Thr Asp Val Asn Glu Cys Asp Val Asn Gly Phe Thr Ala Phe
            115                 120                 125

Met Glu Ala Ala Val Tyr Gly Lys Val Glu Ala Leu Arg Phe Leu Tyr
        130                 135                 140

Asn Asn Gly Ala Glu Val Asn Leu His Arg Lys Thr Ile Glu Asp Gln
145                 150                 155                 160

Glu Arg Val Lys Lys Gly Gly Ala Thr Ala Leu Met Asp Ala Ala Arg
                165                 170                 175

Arg Gly His Val Asp Val Val Glu Ile Leu Leu His Glu Met Gly Ala
                180                 185                 190

Asp Val Asn Ala Arg Asp Asn Arg Gly Arg Asn Ala Leu Ile Tyr Ala
            195                 200                 205

Leu Leu Asn Ser Asp Asp Glu Lys Val Lys Val Lys Ala Thr Thr Arg
        210                 215                 220

Leu Leu Leu Asp Tyr Lys Val Asp Val Asn Val Arg Gly Glu Gly Arg
225                 230                 235                 240

Lys Thr Pro Leu Ile Leu Ala Val Glu Lys Lys Asn Leu Asp Leu Val
                245                 250                 255

Gln Met Leu Leu Glu Gln Thr Ala Ile Glu Ile Asn Asp Thr Asp Ser
            260                 265                 270

Glu Gly Lys Thr Ala Leu Leu Leu Ala Val Glu Leu Lys Leu Lys Glu
        275                 280                 285

Ile Ala Gln Leu Leu Cys Arg Lys Gly Ala Ser Thr Lys Cys Gly Asp
    290                 295                 300

Leu Val Ala Ile Ala Lys Arg Asn Tyr Asp Ser Asp Leu Ala Lys Phe
305                 310                 315                 320

Leu Arg Gln His Gly Ala Val Glu Asp Val Cys Pro Ala Lys Ala
                325                 330                 335

Trp Lys Pro Gln Ser Ser Arg Trp Gly Glu Ala Leu Lys His Leu His
                340                 345                 350

Arg Ile Tyr Arg Pro Met Ile Gly Lys Leu Lys Ile Phe Ile Asp Glu
            355                 360                 365

Glu Tyr Lys Ile Ala Asp Thr Ser Gln Gly Gly Ile Tyr Leu Gly Leu
        370                 375                 380

Tyr Glu Glu Gln Glu Val Ala Val Lys Arg Phe Pro Lys Gly Ser Thr
385                 390                 395                 400
```

```
Arg Gly Gln Asn Glu Val Ser Cys Leu Gln Ser Asn Arg Ala Asn Gly
                405                 410                 415
His Val Val Thr Phe Tyr Gly Ser Glu Ser Asp Arg Thr Cys Leu Tyr
            420                 425                 430
Val Cys Leu Ala Leu Cys Glu His Thr Leu Glu Lys His Leu Asp Asp
        435                 440                 445
Arg Lys Gly Glu Ala Val Gln Asn Lys Glu Asp Glu Phe Ala Arg Asn
    450                 455                 460
Ile Leu Ser Ser Leu Phe Lys Ala Val Glu Glu Leu His Arg Ser Gly
465                 470                 475                 480
Tyr Thr His Gln Asp Leu Gln Pro Gln Asn Ile Leu Ile Asp Ser Lys
                485                 490                 495
Asn Gly Ala Cys Leu Ala Asp Phe Asp Lys Ser Val Lys Gly Thr Gly
                500                 505                 510
Asp Pro Gln Glu Ile Lys Arg Asp Leu Glu Ala Leu Gly Leu Leu Val
            515                 520                 525
Leu Tyr Val Val Lys Lys Gly Asn Asp Ser Phe Glu Met Leu Lys Asn
        530                 535                 540
Leu Arg Thr Glu Glu Leu Ile Glu Arg Ser Pro Asp Lys Glu Thr Arg
545                 550                 555                 560
Asp Leu Ile Arg His Leu Leu Val Pro Gly Asp Asn Val Lys Gly His
                565                 570                 575
Leu Ser Gly Leu Leu Ala His Pro Phe Phe Trp Ser Trp Glu Ser Arg
                580                 585                 590
Tyr Arg Thr Leu Arg Asp Val Gly Asn Glu Ser Asp Ile Lys Thr Arg
            595                 600                 605
Asn Thr Asn Gly Lys Ile Leu Gln Leu Leu Gln Pro Glu Thr Ser Glu
            610                 615                 620
Leu Pro Ser Phe Ala Gln Trp Thr Ile Glu Val Asp Lys Ser Val Met
625                 630                 635                 640
Lys Lys Met Asn Thr Tyr Gln Asn Thr Val Gly Asp Leu Leu Lys Phe
                645                 650                 655
Ile Arg Asn Val Gly Glu His Ile Asn Glu Gln Lys Asn Ile Glu Met
                660                 665                 670
Lys Ser Lys Ile Gly Glu Pro Ser Gln Tyr Phe Gln Glu Lys Phe Pro
        675                 680                 685
Asp Leu Val Met Tyr Val Tyr Lys Arg Leu Gln Asn Thr Glu Tyr Ala
    690                 695                 700
Lys His Phe Pro Lys Asn Leu Asn Leu Asn Lys Pro Asp Val
705                 710                 715
```